US008338572B2

(12) United States Patent
Scuderi et al.

(10) Patent No.: US 8,338,572 B2
(45) Date of Patent: Dec. 25, 2012

(54) KITS FOR BIOMARKER DETECTION AND TREATMENT SELECTION

(75) Inventors: Gaetano J. Scuderi, Jupiter, FL (US); Lewis S. Hanna, Naples, FL (US); Robert Bowser, Cranberry Township, PA (US)

(73) Assignee: Cytonics Corporation, Jupiter, FL (US)

( * ) Notice: Subject to any disclaimer, the term of this patent is extended or adjusted under 35 U.S.C. 154(b) by 373 days.

(21) Appl. No.: 12/570,279

(22) Filed: Sep. 30, 2009

(65) Prior Publication Data

US 2010/0098684 A1 Apr. 22, 2010

Related U.S. Application Data

(60) Provisional application No. 61/106,059, filed on Oct. 16, 2008, provisional application No. 61/118,401, filed on Nov. 26, 2008, provisional application No. 61/122,045, filed on Dec. 12, 2008.

(51) Int. Cl.
*C07K 16/18* (2006.01)
*C07K 14/435* (2006.01)

(52) U.S. Cl. ..................................... 530/387.1; 530/350

(58) Field of Classification Search ........................ None
See application file for complete search history.

(56) References Cited

U.S. PATENT DOCUMENTS

| | | | |
|---|---|---|---|
| 4,391,904 | A | 7/1983 | Litman et al. |
| 4,946,778 | A | 8/1990 | Ladner et al. |
| 5,387,504 | A | 2/1995 | Mumford et al. |
| 5,427,954 | A | 6/1995 | Sandy et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,866,007 | A | 2/1999 | Whitson et al. |
| 5,935,796 | A | 8/1999 | Fosang |
| 6,267,722 | B1 | 7/2001 | Anderson et al. |
| 6,326,162 | B1 | 12/2001 | Miller et al. |
| 6,329,511 | B1 | 12/2001 | Vasquez et al. |
| 6,451,575 | B1 | 9/2002 | Arner et al. |
| 6,506,559 | B1 | 1/2003 | Fire et al. |
| 6,656,745 | B1 | 12/2003 | Cole |
| 6,818,455 | B2 | 11/2004 | May et al. |
| 7,049,412 | B1 | 5/2006 | Arner et al. |
| 7,094,590 | B2 | 8/2006 | Yamajii et al. |
| 7,183,930 | B2 | 2/2007 | Basir et al. |
| 7,189,522 | B2 | 3/2007 | Esfandiari |
| 7,223,834 | B2 | 5/2007 | Miller et al. |
| 7,612,181 | B2 | 11/2009 | Wu et al. |
| 2003/0138404 | A1 | 7/2003 | Maroun |
| 2004/0115629 | A1 | 6/2004 | Panzer et al. |
| 2004/0203072 | A1 | 10/2004 | Sandell et al. |
| 2005/0152905 | A1 | 7/2005 | Omoigui |
| 2006/0188885 | A1 | 8/2006 | Bodian et al. |
| 2006/0204968 | A1 | 9/2006 | Haeupl et al. |
| 2007/0099246 | A1 | 5/2007 | Sandy et al. |
| 2007/0122405 | A1 | 5/2007 | Roschke et al. |
| 2007/0292892 | A1 | 12/2007 | Sandell et al. |
| 2008/0188642 | A1 | 8/2008 | Ying et al. |
| 2009/0291462 | A1 | 11/2009 | Sumer et al. |
| 2009/0299769 | A1 | 12/2009 | Dam et al. |

FOREIGN PATENT DOCUMENTS

JP 2004 256436 9/2004

OTHER PUBLICATIONS

Aigner et al., "Anabolic and Catabolic Gene Expression pattern analysis in Normal versus osteoarthritic Cartilage Using Complementary DNA-array Technology", Arthritis Rheum., Dec. 2001, 44(12), 2777-2789.

Dahlberg et al., "A Longitudinal Study of Cartilage Matrix Metabolism in Patients with Cruciate Ligament Rupture-Synovial Fluid Concentrations of Aggrecan Fragments, Stromelysin-1 and Tissue Inhibitor of Metalloproteinase-1", Br. J. Rheumatol, Dec. 1994, 33(12), 1107-1111.

El-Sayed et al., "Cartilage Proteoglycan Aggrecan as a Predictor of Joint Damage in Juvenile Rheumatoid Arthritis", East Mediterr Health J., Nov. 2001, 7(6), 992-1003.

Guehring et al., "Stimulation of Gene Expression and Loss of Anular Architecture Caused by Experimental disc Degeneration—an in Vivo Animal Study", Spine (Philadelphia 1976), Nov. 15, 2005, 30(22), 2210-2015.

Larsson et al., "Synovial Fluid Level of Aggrecan ARGS Fragments is a more Sensitive Marker of Joint Disease than Glycosaminoglycan or Aggrecan Levels: A Cross-Sectional Study", Arthritis Res. Ther., Jun. 22, 2009 11(3), 11 pages.

Lohmander et al., "Changes in Joint Cartilage Aggrecan after Knee Injury and in Osteoarthritis", Arthritis Rheum, Mar. 1999, 42(3), 534-544.

Lohmander et al., "Longitudinal and Cross-Sectional Variability in markers of Joint Metabolism in Patients with Knee Pain and Articular Cartilage Abnormalities", Osteoarthritis Cartilage, Sep. 1998, 6(5), 351-361.

Mazzuca et al., "Associations between Joint Space Narrowing and Molecular Markers of Collagen and Proteoglycan Turnover in Patients with Knee Osteoarthritis", Rheumatol, Jun. 2006, 33(6), 1147-1151.

Messner et al., "Synovial Reaction and Concentrations of Proteoglycan Fragments in Joint Fluid after Intraarticular Knee Injuries", Journal Knee Surgery Sport Traumatology, Arthroscopy, Jul. 1995, 3(2), 4 pages.

Ratcliffe et al., "Biochemical Markers in Synovial Fluid Identify Early Osteoarthritis of the Glenhumeral Joint", Clin. Orthop Res., Sep. 1996, 330, 45-53.

(Continued)

*Primary Examiner* — Christine J Saoud
*Assistant Examiner* — Jon M Lockard
(74) *Attorney, Agent, or Firm* — Woodcock Washburn LLP

(57) ABSTRACT

Biomarkers, including isolated fibronectin-aggrecan complexes that correlate with spinal or joint pain and inflammation, and methods for their detection are provided. Also provided are methods for identifying treatment sites in the spine or joint for treatment of pain and inflammation by detecting the presence of, or increased levels of, fibronectin-aggrecan complexes. Methods for treating spinal or joint pain and inflammation are also provided.

12 Claims, 4 Drawing Sheets

OTHER PUBLICATIONS

Struglics et al., "Human Osteoarthritis Synovial Fluid and Joint Cartilage Contain both Aggrecanase and Matrix Metalloproteinase-Generated Aggrecan Fragments", Osteoarthritis Cartilage, Feb. 2006, 14(2), 13 pages.

Struglics et al., "Western Blot Quantification of Aggrecan Fragments in Human Synovial Fluid Indicates Differences in Fragment Patterns Between Joint Disease", Osteoarthritis Cartilage, Apr. 2009, 17(4), 497-506.

Sugimoto et al., "Intraarticular Injection of Molecular weight Hyaluronan for Osteoarthritis of the Knee-Prediction of Effectiveness with Biological Markers", J. Rheumatol, Dec. 2006, 33(12), 5 pages.

Tsuritani et al., "Cytokine Receptor-Like Factor 1 is Highly Expressed in Damaged Human Knee Osteoarthritic Cartilage and Involved in Osteoarthritis Downstream of TGF-beta", Calcif Tissue Int., Nov. 17, 2009, 11 pages.

Zack et al., "Identification of Fibronectin Neoepitopes Present in Human Osteoarthritic Cartilage", Arthritis & Rheumatism, Aug. 31, 2006, 54(9), 2912-2922.

ACAN aggrecan [*Homo sapiens*] NCBI Reference Sequence NM_001135.3, pp. 1-7, updated Apr. 5, 2010, accessed Apr. 5, 2010.

Anderson, et al., "A fibronectin fragment alters the metabolism by rabbit intervertebral disc cells in vitro", *Spine* (Phila Pa 1976), 30(11):1242-6 (2005).

Anderson, et al., "A fibronectin fragment stimulates intervertebral disc degeneration in vivo", *Spine* (Phila Pa 1976) 28(20):2338-45 (2003).

Barilla and Carsons et al., "Fibronectin fragments and their role in inflammatory arthritis", *Seminars in Arthritis and Rheumatism*, 29:4252-265 (2000).

Burton-Wurster and Lust, "Fibronectin and water content of articular cartilage explants after partial depletion of proteoglycans", *Journal of Orthopaedic Research*, 4:4437-455 (1986).

De Grauw, et al., "Arthrogenic lameness of the fetlock: synovial fluid markers of inflammation and cartilage turnover in relation to clinical joint pain", *Equine Veterinary Journal*, 38(4):305-311 (2006) (abstract only).

De Jager, et al., "Simultaneous detection of 15 human cytokines in a single sample of stimulated peripheral blood mononuclear cells", *Clin. Diagn. Lab. Immunol.*, 10(1):133-9 (2003).

FN1 fibronectin 1 [*Homo sapiens*] NCBI Reference Sequence NM_212476.1, pp. 1-11, updated Mar. 28, 2010, accessed Apr. 5, 2010.

Hashimoto, et al., "ADAMTS4 (aggrecanase-1) interaction with the c-terminal domain of fibronectin inhibits proteolysis of aggrecan", *Journal of Biological Chemistry*, 27(31): 32483-32491 (2004).

Moseley, et al., "A controlled trial of arthroscopic surgery for osteoarthritis of the knee", *N. Engl. J. Med.*, 347(2):81-8 (2002).

Oegema, et al., "Fibronectin and its fragments increase with degeneration in the human intervertebral disc", Spine (Phila Pa 1976) 1;25(21):2742-7 (2000).

Sato, et al., "Relationship of calcitonin gene-related peptide in synovial tissues and temporomandibular joint pain in humans", *Oral Surgery, Oral medicine, Oral Pathology, Oral Radiology Andendodontics*, (98)5: 533-540 (2004).

Scuderi, et al., "A critical evaluation of discography in patients with lumbar intervertebral disc disease", *Spine J.*, 8(4):624-9 (2008). Epub Jan. 10, 2007.

Scuderi, et al., "Cytokine assay of the epidural space lavage in patients with lumbar intervertebral disk herniation and radiculopathy", *J. Spinal Disord. Tech.*, 19(4):266-9 (2006).

Struglics, et al., "Human osteoarthritis synovial fluid and joint cartilage contain both aggrecanase- and matrix metalloproteinase-generated aggrecan fragments", *Osteoarthritis and Cartilage*, 14(2): 101-113 (2006).

Zack, et al., "Identification of fibronectin neoepitopes present in human osteoarthritic cartilage", *Arthritis and Rheumatism*, 54:9, 2912-2922 (Sep. 2006).

Zhang, et al., "Characterization of fibronectin fragments in human surgical intervertebral disk specimens", Academy Annual Assembly Abstracts, Poster 108, *Arch. Phys. Med. Rehabil.* 88:E40 (2007).

KITS FOR BIOMARKER DETECTION AND TREATMENT SELECTION

CROSS-REFERENCE TO RELATED APPLICATIONS

This application claims benefit of and priority to U.S. Provisional Patent Application Nos. 61/106,059 filed on Oct. 16, 2008, and 61/118,401 filed on Nov. 26, 2008, and 61/122,045 filed on Dec. 12, 2008 all of which are by Gaetano J. Scuderi, Lewis S. Hanna, and Robert Bowser, and are incorporated by reference in their entirety.

FIELD OF THE INVENTION

The invention is generally related to methods for diagnosing pathologies associated with spinal- or joint-related pain as well as compositions and methods for treating spinal- or joint-related pain.

BACKGROUND OF THE INVENTION

Spinal and joint pain can be difficult to treat. In particular the cause of spinal and joint pain can be difficult to identify. Increasing degrees of force applied to joints result in joint injury. Abnormal joint anatomy is frequently a hallmark of ageing, but joint injury is also frequently seen as a result of trauma. For instance, chondral lesions are often seen in athletes. While joint injury resulting from trauma is typically associated with acute inflammation, aberrant joint anatomy resulting from ageing (e.g., osteoarthritis) is a chronic condition. Physicians currently do not have a system or method available to differentiate between acute injury due to trauma and age related joint deteriorations. It is presently difficult to determine the appropriate course of treatment for a given patient since it is frequently unclear whether the particular condition the patient suffers from is acute or chronic.

The exceedingly high rate of exploratory knee arthroscopy highlights the difficulty of diagnosing meniscal injury. This problem is exacerbated by the low specificity of MRI, currently a mainstay of diagnosing this pathology. It has been shown that MRI will identify a meniscal injury in as many as 65% of asymptomatic people making MRI a questionable diagnostic tool and highlighting the lack of correlation between abnormal meniscal anatomy and knee pain. Lack of a clear correlation between abnormal meniscus anatomy and knee pain is particularly problematic in the elderly patient population many of whom develop osteoarthritis. Despite the overwhelming evidence questioning its utility (Moseley, et al., *N. Engl. J. Med.,* 347(2):81-8 (2002)), knee arthroscopy is still performed an estimated 660,000 times per year in the U.S. alone (AAOS website).

Spinal-related pain is typically classified as discogenic, facetogenic or radiculopathic pain. The manifestation of radiculopathic pain has traditionally been attributed to various physical/mechanical abnormalities, such as compression or mechanical irritation of the nerve root related to conditions such as disk herniation, stenosis, spondylolisthesis, sciatica, Piriformis Syndrome, Obturator Syndrome, cystic lesions (e.g., ganglion and synovial), tumors, and other pathology.

It has been demonstrated that the application of nucleus pulposus to the spinal nerve root can result in axonal damage and functional changes to nerve root micro-anatomy, resulting in pain-related behaviors. Thus, it has been theorized that a mechanical defect releasing the nucleus pulposus into the epidural space may cause nerve root damage resulting in radicular pain. This "chemical radiculopathy" may explain the presence of radiculopathic pain in only a portion of a patient population that has mechanical failures such as disk herniation, while the remaining patients remain pain-free.

Numerous studies have attempted to elucidate the pathophysiology of spinal-related pain, and several molecular pathways have been implicated tentatively. However, no clear causal pathway leading from injury or degeneration to the painful state has been confirmed. Molecular markers may be linked to clinical symptoms, and serve as potential targets for the development of diagnostics and therapeutic tools. Although some studies have provided evidence that the epidural space may be affected by an intervertebral disk herniation, none has measured concentrations of biomolecules in the epidural space in an attempt to detect the differences between affected and non-affected persons.

Therefore, it is an object of the invention to provide biomarkers that are indicative of pain in the spine or joint.

It is another object of the invention to provide biomarkers and methods for identifying sites in the spine or joint for treating pain.

It is another object of the invention to provide biomarkers that may be used to diagnose or assist in the diagnosis of the presence of pathologies that are causative of spinal- or joint-related pain.

It is another object of the invention to provide methods for diagnosing or assisting in the diagnosis of the presence of pathologies that are causative of spinal- or joint-related related pain.

It is yet another object of the invention to provide biomarkers and methods to determine an appropriate therapy for a subject experiencing spinal- or joint-related pain.

It is yet another object of the invention to provide biomarkers and methods to monitor and assess the efficacy of a treatment for spinal- or joint-related pain.

It is still another object of the invention to provide compositions and methods for treating spinal or joint pain.

It is still another object to provide methods and compositions for selecting treatment sites in the spine or joint for treatment to inhibit or reduce pain.

SUMMARY OF THE INVENTION

Biomarkers that correlate with spinal and/or joint pain have been identified. Biomarkers include complexes or aggregates that contain fibronectin and aggrecan polypeptides, or fragments thereof. In some embodiments, fibronectin-aggrecan complexes contain the G1, G2, or G3 domain of aggrecan, fibronectin binding fragments thereof, or combinations thereof.

Methods for identifying treatment sites in the spine or joint for treatment of pain by detecting the presence of, or increased levels of, fibronectin-aggrecan complexes in a spinal or joint sample, are also provided. In some embodiments, the site that is identified as a treatment site is also a site that is a source of spinal or joint pain. Spinal samples may be obtained by any suitable method, including, but not limited to, epidural lavage, disc space lavage and facet joint lavage. Joint samples can be obtained using conventional methods including, but not limited to, percutaneous or open aspiration, biopsy or lavage. Complexes containing fibronectin and aggrecan may be detected using any suitable method, including, but not limited to, chromatographic methods, selective binding assays, mass spectrometry, spectrophotometry, or combinations thereof. In one embodiment, complexes containing fibronectin and aggrecan can be isolated from spinal samples, the epidural space, or cerebrospinal fluid.

Selective binding assays that may be used for the detection of fibronectin-aggrecan complexes use selective binding partners for fibronectin, aggrecan, or fragments or complexes. Useful selective binding partners include antibodies and polypeptides that are known in vivo binding partners for fibronectin and aggrecan. Exemplary selective binding assays include Western blotting, immunoprecipitation, ELISA and radioimmunoassay. Particularly preferred binding assays include assays that selectively detect complexes containing fibronectin and aggrecan without significantly detecting fibronectin or aggrecan not present in fibronectin-aggrecan complexes.

A positive control for detecting fibronectin-aggrecan complexes in the disclosed detection assays is also provided. The positive control or Reference Standard is typically a fibronectin-aggrecan complex wherein the fibronectin and aggrecan are from the same or different species with sequences homologous to human sequences.

The disclosed methods for detecting fibronectin-aggrecan complexes are useful to diagnose, or assist in the diagnosis of, pain syndromes related to the anatomic structure and physiologic function of the spine or joint. Detection of fibronectin-aggrecan complexes in samples from specific locations within the spine may be used to diagnose, or assist in the diagnosis of, radiculopathy, facet joint pain, discogenic pain, or joint pain. The presence of fibronectin-aggrecan complexes may also be used to designate a particular subject for a treatment, to determine a prognosis for a subject, or to monitor the efficacy of a treatment for spinal or joint pain in a subject.

Methods for treating spinal or joint pain are also provided. The methods include treating a painful site of a subject which is identified by detection of the presence of, or increased levels of fibronectin-aggrecan complexes. Suitable treatment methods include any known in the art including, but not limited to, surgical methods of spinal decompression, and treatment with steroidal and non-steroidal anti-inflammatory agents.

Other methods for treating spinal or joint pain include administering antagonists of fibronectin-aggrecan complexes. Suitable fibronectin-aggrecan complex antagonists inhibit or reduce one or more biological activities of fibronectin-aggrecan complexes, inhibit or reduce the formation of fibronectin-aggrecan complexes from fibronectin and aggrecan and/or their fragments, cause the dissociation of fibronectin-aggrecan complexes, reduce the expression of fibronectin and/or aggrecan, or reduce the degradation and the breakdown of aggrecan from cartilage. Exemplary fibronectin-aggrecan complex antagonists include, but are not limited to, antibodies and other polypeptides, peptidomimetics, small organic molecules, and inhibitory RNAs, such as ribozymes, triplex-forming oligonucleotides, antisense DNA, siRNA and miRNA.

DETAILED DESCRIPTION OF THE INVENTION

I. Definitions

Figure 1:
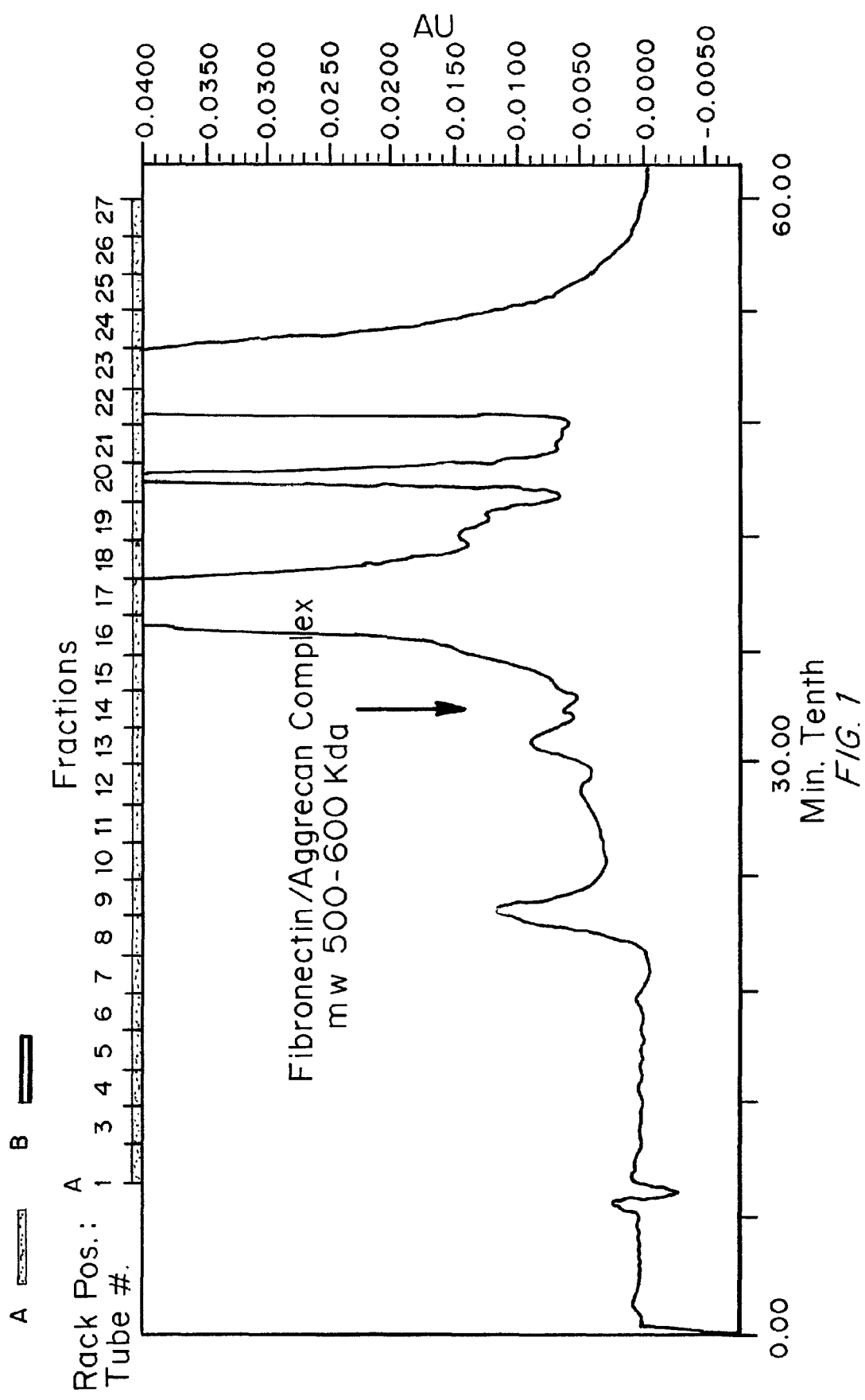
FIG. 1 is a graph showing the results of size exclusion chromatography (SEC) of a symptomatic human sample. The graph expresses the optical density of proteins at 215 nm eluted from the SEC column as a function of elution time in minutes. The arrow identifies the Fibronectin/aggrecan G3 fragment peak detected by the assay. The other high molecular weight peaks contain complexes of fibronectin with other or bigger fragments of aggrecan.

As used herein, the terms "radicular pain", "radiculopathy", radiculopathic pain" and "sciatica" refer to radiating pain of the extremities which emanates from the spinal root level or "radic" along the path of one or more irritated lumbar nerve roots. In the case of sciatica, this would originate from the L4, L5 and/or Si spinal nerve roots, which make up the sciatic nerve. Radiating pain is also possible from the high lumbar disk herniations in the L3, L2 or L1 regions or from any cervical nerve root in the case of a cervical disk herniation, cervical nerve root irritation or cervical disk degeneration. This pain differs from pain resulting from a facet joint or other spinal structure, which is classified as "referred" pain. Radiating pain is also possible from the high lumbar disc herniations in the L3, L2 or L1 regions or cervical spine regions.

As used herein, "discogenic pain" refers to spinal-related pain that generates from an intervertebral disk. The intervertebral disk suffers from reduced functionality in association with a loss of hydration from the nucleus pulposus. The reduction in functionality coincides with damage in the annulus fibrosus. This weakening can lead to anatomic lesions such as bulging, prolapsed, extruded, or sequestered disc. This weakening can also lead to possible biochemical lesions resulting from leakage of the disk contents that may manifest in back pain or aforementioned chemical radiculopathy.

As used herein, "facet joint pain" or "facetogenic pain" refers to pain generating from the facet joint. "Facet joints" or "zygapophysial joints" are paired, true synovial joints endowed with cartilage, capsule, meniscoid, and synovial membrane.

As used herein the term "spinal-pain" or "spine related pain" includes discogenic, facetogenic and radiculopathic pain.

As used herein, the term "acute pain" refers to pain lasting up to six months, e.g., five months, four months, three months, two months, four weeks, three weeks, two weeks, one week, six days, five days, four days, three days, two days or one day or less.

As used herein, the term "chronic pain" refers to pain of a duration of longer than six months.

As used herein, "biological sample" refers to a cell or population of cells or a quantity of tissue or fluid from a patient. Such samples are typically from humans, but include tissues isolated from non-human primates, rodents, e.g., mice, and rats, caprines, bovines, canines, equines and felines. Biological samples may also include sections of tissues such as biopsy samples, frozen sections taken for histologic purposes, and lavage samples.

As used herein, the terms "spine sample" or "sample from the spine" refer to samples of tissue or fluid from the spine including, but not limited to, "spinal disk samples", "epidural samples" and "facet joint samples". Frequently, these samples are also referred to as "biological samples".

As used herein, the term "joint" or "joint of the appendicular skeleton" refers to any diarthoidal joint. Diarthoidal joints are also referred to as synovial joints. The term "joint" therefore refers to any joint containing bone, articular cartilage, a joint capsule, a synovial tissue lining, and lubricating synovial fluid inside the capsule. The term "chondral" refers to the cartilage components of a joint. The term "meniscus" or "meniscal" typically refers to a component of the knee.

As used herein, the terms "normal joint" or "control joint" refer to a joint that is an insignificant source of pain to a subject. The level of pain that may be present in a normal joint typically does not impact the function or quality of the patient's life to the degree that the patient seeks medical care.

As used herein, the terms "joint sample" or "sample from a joint" refer to samples of tissue or fluid from a joint including, but not limited to, synovial fluid samples and joint or tissue lavages, ex vivo and in vivo. Frequently, these samples are also referred to as "biological samples".

As used herein, the phrases "level of a biomarker" or "level of fibronectin-aggrecan complex" or "level of fibronectin-aggrecan G3 complex" in a biological sample refers to the amount of the biomarker that is present in a biological sample. The "level of a biomarker" or "level of fibronectin-aggrecan complex" or "level of fibronectin-aggrecan G3 complex" need not be quantified, but can simply be detected, e.g., a subjective, visual detection by a human, with or without comparison to a level from a control sample or a level expected of a control sample.

The terms "polypeptide", "peptide" and "protein" are used interchangeably herein to refer to a polymer of amino acid residues. The terms apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers.

The term "agent" or "therapeutic agent" is used to describe a compound that has or may have a pharmacological activity. Agents include compounds that are known drugs, compounds for which pharmacological activity has been identified but that are undergoing further therapeutic evaluation, and compounds that are members of collections and libraries that are to be screened for a pharmacological activity. The term includes an organic or inorganic chemical such a peptide, including antibodies, proteins and small molecules and natural products.

As used herein, the term "immunoassay" refers to an assay that uses an antibody or antibodies to specifically bind an antigen. The immunoassay is characterized by the use of specific binding properties of a particular antibody or antibodies to detect, quantify, and/or target the antigen.

"Specific binding" between a binding agent, e.g., an antibody and a protein, for instance, a biomarker, refers to the ability of a capture- or detection-agent to preferentially bind to a particular that is present in a mixture; e.g., a biological sample. Specific binding also means a dissociation constant ($K_D$) that is less than about $10^{-6}$ M; preferably, less than about $10^{-8}$ M; and, most preferably, less than about $10^{-9}$ M.

The phrase "specifically (or selectively) binds" to an antibody or "specifically (or selectively) immunoreactive with" when referring to a protein or peptide, refers to a binding reaction that is determinative of the presence of the protein in a heterogeneous population of proteins and other biologics. Thus, under designated immunoassay conditions, the specified antibodies bind to a particular protein or protein complex at least two times the background and do not substantially bind in a significant amount to other proteins present in the sample.

As used herein, a "label" or a "detectable moiety" is a composition detectable by spectroscopic, photochemical, biochemical, radiographic, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into nucleic acids, proteins and antibodies at any position. Any method known in the art for conjugating the antibody to the label may be employed, e.g., using methods described in Hermanson, Bioconjugate Techniques 1996, Academic Press, Inc., San Diego.

As used herein, the terms "inhibitors" or "antagonists" refers to compounds or compositions that directly or indirectly partially or totally block activity, decrease, prevent, delay activation, inactivate, desensitize, or down regulate the activity or expression of the targeted biomarker. Antagonists are, for example, polypeptides, such as antibodies, and soluble receptors, as well as nucleic acids such as siRNA or antisense RNA, as well as naturally occurring and synthetic biomarker antagonists, including small chemical molecules.

II. Biomarkers of Spinal or Joint Pain

Biomarkers that are indicative of pain in the spine or joint have been empirically determined. In several embodiments, the biomarker includes a complex of fibronectin with aggrecan, preferably a complex of fibronectin with aggrecan isolated from a spinal sample or a joint sample. The examples below demonstrate that a biomarker that includes a complex of fibronectin and aggrecan is present in biological samples from the spine or a joint in subjects experiencing spinal or joint pain.

The biomarker may contain fibronectin and aggrecan polypeptides in any ratio. The complex may include full length fibronectin and aggrecan polypeptides or may include fragments of fibronectin and/or aggrecan polypeptides. The term "fragment" refers to any subset of the polypeptide that is a shorter polypeptide of the full length protein. Exemplary fragments of fibronectin or aggrecan include 20, 30, 40, 50 or more amino acids from fibronectin or aggrecan that can be detected with anti-fibronectin or anti-aggrecan antibodies, respectively. Other exemplary fragments of aggrecan include portions of aggrecan polypeptides that contain one or more of the G1, IGD, G2, KS, CS1, CS2 or G3 domains of aggrecan, or fragments or combinations thereof. In one embodiment, the biomarker includes a complex of fibronectin or a fragment thereof with the G3 domain of aggrecan or a fragment thereof. In other embodiments, the biomarker includes a complex of fibronectin or a fragment thereof with the G1 or G2 domain of aggrecan or fragments thereof.

An exemplary human fibronectin 1 sequence can be found under the NCBI gene ID 2335 (FN1; Ensembl: ENSG00000115414; HPRD:00626; MIM:135600). "Fibronectin", as used herein, also includes any naturally-occurring fibronectin variants including approximately 20 known splice variants associated with a disease or a disorder and fibronectin variants due to different splicing by different cell types.

Aggrecan is a member of the chondroitin sulfate proteoglycan family, which also includes versican, brevican and neurocan. An exemplary aggrecan 1 sequence can be found under the NCBI gene ID 176 (ACAN; Ensembl: ENSG00000157766; HPRD:01123; MIM:155760). Exemplary versican sequence can be found under the NCBI gene ID (VCAN; Ensembl: ENSG00000038427; UniProtKB: P13611). Exemplary brevican sequence can be found under NCBI gene ID (BCAN; Ensembl: ENSG00000132692; UniProtKB: Q96GW7). Exemplary neurocan sequence can be found under the NCBI gene ID (NCAN; Ensembl: ENSG00000130287; UniProtKB: O14594). This gene family is highly homologous and exhibits similar protein functions containing extensive protein domains of greater than 50% amino acid identity. "Aggrecan", as used herein also includes any naturally-occurring variants and splice variants of aggrecan, versican, brevican and neurocan, and any variants of aggrecan, versican, brevican and neurocan due to splicing by different cell types.

The fibronectin or aggrecan polypeptides, or fragments thereof, can also be variants, or post-translationally modified variants of fibronectin or aggrecan. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids. A variant polypeptide can have any combination of amino acid substitutions, deletions or insertions. In one embodiment, fibronectin or aggrecan variant polypeptides have an integer number of amino acid alterations such that their amino acid sequence shares at least 60, 70, 80, 85, 90, 95, 97, 98, 99, 99.5 or 100% identity with an amino acid sequence of a wild type fibronectin or aggrecan polypeptide. In a preferred embodiment, fibronectin and aggrecan variant polypeptides have an amino acid sequence sharing at least 60, 70, 80, 85, 90, 95, 97, 98, 99, 99.5 or 100% identity with the amino acid sequence of a wild type fibronectin or aggrecan polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.*, 48:443-453 (1970)); 2) BLOSSUM62 comparison matrix from Hentikoff and Hentikoff (*Proc. Natl. Acad. Sci. USA.*, 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

III. Methods for Identifying a Treatment Site for Treating Spinal or Joint Pain Methods for determining a treatment site for treating spinal pain or joint pain by detecting the presence or levels of fibronectin-aggrecan complexes are disclosed.

A. Spinal Pain

The detection of the presence of, or increased levels of, a complex of fibronectin and aggrecan at a site within the spine may be used to identify that site as a site in need of treatment for spinal pain. In some embodiments, a site that is determined to be a site for treating spinal pain based on the presence of, or increased levels of, fibronectin-aggrecan complexes, is also a site that is a source of pain. In some embodiments, the proposed methods include obtaining one or more biological samples from levels of the spine suspected of being a source of pain and detecting and comparing the levels of a fibronectin-aggrecan complexes in each of the biological samples. This should be useful in identifying the actual painful site, rather than sites of referred pain. Suitable subjects to be tested for the presence of, or increased levels of, fibronectin-aggrecan complexes include any subject presenting with pain in the spine. Subjects may be experiencing pain that is suspected of being, for example, discogenic, facetogenic or radicular pain.

The disclosed methods are useful to determine locations in the spine for treating spinal pain. These locations may also be sites in the spine that are a source of pain. The identification of the site that is causing a subject pain is useful to diagnose, or assist in the diagnosis of a pathology or injury in the subject. The identification of the site that is causing a subject pain is also useful to assist in the determination of a proper treatment for the affected subject.

B. Joint Pain

The detection of the presence of or increased levels of a complex of fibronectin and aggrecan within a joint may be used to identify that joint as a site for treating joint pain. In some embodiments, a site that is determined to be a site for treating joint pain based on the presence of, or increased levels of fibronectin-aggrecan complexes, is also a site that is a source of pain. In some embodiments, the proposed methods include obtaining one or more biological samples from joints suspected of being a source of pain and detecting the levels of a fibronectin-aggrecan complexes in the biological samples. Suitable subjects to be tested for the presence of, or increased levels of, fibronectin-aggrecan complexes include any subject presenting with pain in a joint of the appendicular skeleton. Subjects may be experiencing pain that is suspected of being, osteoarthritis, chondrosis, or related to meniscal, tendon or ligament pathology, for example.

The disclosed methods are useful to determine treatment sites for treating joint pain. These locations may also be joints that are a source of pain. The identification of a joint that is causing a subject pain is useful to diagnose, or assist in the diagnosis of a pathology or injury in the subject. The identification of a joint that is causing a subject pain is also useful to assist in the determination of a proper treatment for the affected subject.

C. Subjects

Subjects that may be selected for the detection of fibronectin-aggrecan complexes include any subject that presents with pain in the spine or joint. Preferably the subject is human. Subjects may be experiencing any pain associated with the spine, including, but not limited to, discogenic, facetogenie or radiculopathic pain.

Suitable subjects may be suspected of experiencing pain associated with any anatomic structure of a joint including, but not limited to, bone, articular cartilage, or the synovial tissue lining. Joints may include, but are not limited to, large diarthrodial (synovial) joints (e.g. knee, hip, shoulder), small diarthrodial (synovial) joints (e.g. elbow, wrist, ankle, zygoapophyseal or facet joints of spine), and amphiarthrodial joints (e.g. sacroiliac joint, sternoclavicular joint, tempomandibular joint ("TMJ")). Subjects may be experiencing acute joint-related pain, or may suffer from chronic joint-related pain.

In one embodiment, the subject has been experiencing joint-related or spine-related pain for 30 or 25 weeks or less. In another embodiment, the subject has been experiencing joint-related or spine-related pain for 20, 15, 10, 8, or 6 weeks, or less.

Subjects may be of either sex and may be of any age. Subjects may be experiencing acute or chronic pain.

D. Detection of Fibronectin-Aggrecan Complexes

1. Methods for Obtaining Biological Samples from the Spine

Any number of methods known in the art can be used to retrieve sample from the spine for the detection of fibronectin-aggrecan complexes. These methods include, but are not limited to, methods for obtaining samples from the epidural space, the intervertebral disk space and the facet joint space. Suitable methods are described in more detail below.

Method 1: Epidural Space Lavage (Caudal)

1) the skin and subcutaneous tissue is infiltrated in the area of introduction that has been verified fluoroscopically;
2) an introducer needle is then inserted through the sacral hiatus, again fluoroscopic confirmation is noted;
3) the catheter is then passed through the needle into the epidural space, utilizing fluoroscopy the catheter is passed to the level of pathology;
4) upon achieving satisfactory position of the catheter the guide wire is removed;
5) a syringe containing approximately 3 cc normal saline (NS) is attached to the distal end of the catheter;
6) ½ cc increments of NS are then injected into the epidural space with an attempt at aspiration with each volume of injectate; three to five seconds is allowed to elapse following each injection prior to re-aspiration;
7) the aspirate is then placed in a microcentrifuge tube containing a protease inhibitor cocktail solution and immediately placed on ice or dry ice or submerged in liquid nitrogen or any other method of rapid freezing;
8) the sample is then transferred to permanent storage at −20° C. or lower until analysis.

Method 2: Epidural (Caudal Sponge)

1) the skin and subcutaneous tissue is infiltrated in the area of introduction that has been verified fluoroscopically;
2) an introducer needle is then inserted through the sacral hiatus, again fluoroscopic confirmation is noted;
3) the catheter is then passed through the needle into the epidural space, utilizing fluoroscopy the catheter is passed to the superior most aspect of the level of pathology;
4) the introducer guide wire is removed and the analyte wire with absorbent material is introduced;
5) a syringe containing 1 cc of normal saline (NS) is attached to the introducer port;
6) NS is then injected soaking the absorbent material;
7) the catheter is then drawn back to the inferior most aspect of the pathology with the absorbent material being drawn over the lesion;
8) the analyte wire is then removed;
9) material is then washed from the absorbent material into a microcentrifuge tube containing a protease inhibitor cocktail solution and immediately placed on ice or dry ice or submerged in liquid nitrogen or any other method of rapid freezing;
10) the microcentrifuge tube is then transferred to permanent storage at −20° C. or lower until analysis. Alternatively, at step nine the sample could then be immediately analyzed utilizing a centralized lab analysis or point of care assay.

Method 3: Transforaminal (Epidural Modification)

1) the skin and subcutaneous tissue is infiltrated in the area of introduction that has been verified fluoroscopically;
2) a small bore needle is then inserted through into the affected foramen, again fluoroscopic confirmation is noted;
3) a syringe containing approximately 1.5 cc normal saline (NS) is attached to the needle;
4) approximately ½ cc increments of NS are then injected into the epidural space with an attempt at aspiration with each volume of injectate, three to five seconds is allowed to elapse following each injection prior to respiration;
5) the aspirate is then placed in a microcentrifuge tube containing a protease inhibitor cocktail solution and immediately placed on ice or dry ice or submerged in liquid nitrogen or any other method of rapid freezing;
6) the microcentrifuge tube is then transferred to permanent storage at −20° C. or lower until analysis.

Method 4: Transforaminal (Ab/Adsorbent Sponge)

1) the skin and subcutaneous tissue is infiltrated in the area of introduction that has been verified fluoroscopically;
2) a needle is then inserted through into the affected foramen; again fluoroscopic confirmation is noted;
3) the analyte wire with absorbent material is introduced through the needle;
4) a syringe containing approximately 1 cc of normal saline (NS) is attached to the needle;
5) NS is then injected to soak the absorbent material;
6) the analyte wire is then removed;
7) the material from the absorbent material is then washed into a microcentrifuge tube containing a protease inhibitor cocktail solution and immediately placed on ice or dry ice or submerged in liquid nitrogen or any other method of rapid freezing;
8) the microcentrifuge tube is then transferred to permanent storage at −20° C. or lower until analysis. Alternatively, at step seven the sample could then be immediately analyzed utilizing a centralized lab or point of care assay.

Method 5: Translaminar 1) the skin and subcutaneous tissue is infiltrated in the area of introduction;
2) a needle is then inserted utilizing an interlaminar approach to the epidural space. A "pop" through the ligamentum flavum will confirm appropriate position in the epidural space, alternatively, fluoroscopic confirmation may be utilized;
3) a syringe containing approximately 3-5 cc of normal saline (NS) is attached to the needle;
4) approximately 1 cc increments of NS are then injected into the epidural space with an attempt at aspiration with each volume of injectate, three to five seconds is allowed to elapse following each injection prior to respiration;
5) the aspirate is then placed in a microcentrifuge tube containing a protease inhibitor cocktail solution and immediately placed on ice or dry ice or submerged in liquid nitrogen or any other method of rapid freezing;

6) the sample is then transferred to permanent storage at −20° C. or lower until analysis.

Method 6: Disk Space (Lavage)

1) the skin and subcutaneous tissue is infiltrated in the area of introduction that has been verified fluoroscopically;

2) utilizing either a single or double needle technique, insertion into the disc space is accomplished under fluoroscopic guidance;

3) a syringe with approximately 1.5 cc of NS is attached to the needle and injected into the disc space;

4) after approximately 3 seconds the disc is re-aspirated for lavage fluid;

5) this may need to be repeated to obtain sufficient fluid (approximately ⅜ cc);

6) the aspirate is then washed into a microcentrifuge tube containing a protease inhibitor cocktail solution and immediately placed on ice or dry ice or submerbed into liquid nitrogen;

7) the microcentrifuge tube is then transferred to permanent storage at −20° C. or lower until analysis.

Method 7: Disk Space (Absorbent Sponge)

1) the skin and subcutaneous tissue is infiltrated in the area of introduction that has been verified fluoroscopically;

2) utilizing either a single or double needle technique, insertion into the disk space is accomplished under fluoroscopic guidance;

3) the introducer guide wire is removed and the analyte wire with absorbent material is introduced;

4) a syringe containing approximately 1 cc of normal saline (NS) is attached to the introducer port;

5) NS is then injected soaking the microcentrifuge tube.

6) the analyte wire is then removed 7) material from the absorbent material is then washed into a microcentrifuge tube containing a protease inhibitor cocktail solution and immediately placed on ice or dry ice or submerbed in liquid nitrogen.

8) the microcentrifuge tube is then transferred to permanent storage at 20° C. or lower until analysis. Alternatively, at step seven the sample could then be immediately analyzed utilizing a centralized lab or point of care assay.

Method 8: Facet Joint Space (Lavage)

1) the skin and subcutaneous tissue is infiltrated in the area of introduction that has been verified fluoroscopically;

2) utilizing either a single or double needle technique, insertion into the facet joint is accomplished under fluoroscopic guidance;

3) a syringe with approximately 1.5 cc of NS is attached to the needle and injected into the facet joint space;

4) after approximately 3 seconds the disc is re-aspirated for lavage fluid;

5) this may need to be repeated to obtain sufficient fluid (approximately ⅜ cc);

6) the aspirate is then washed into a microcentrifuge tube containing a protease inhibitor cocktail solution and immediately placed on ice or dry ice or submerbed into liquid nitrogen;

7) the microcentrifuge tube is then transferred to permanent storage at −20° C. or lower until analysis.

Method 9: Facet Joint Space (Ab/Adsorbent Sponge)

1) the skin and subcutaneous tissue is infiltrated in the area of introduction that has been verified fluoroscopically;

2) utilizing either a single or double needle technique, insertion into the facet joint is accomplished under fluoroscopic guidance;

3) the introducer guide wire is removed and the analyte wire with absorbent material is introduced;

4) a syringe containing approximately 1 cc of normal saline (NS) is attached to the introducer port;

5) NS is then injected soaking the absorbent material;

6) the analyte wire is then removed;

7) material from the absorbent material is then washed into a microcentrifuge tube containing a protease inhibitor cocktail solution and immediately placed on ice or dry ice or submerged in liquid nitrogen; and 8) the microcentrifuge tube is then transferred to permanent storage at −20° C. or lower until analysis. Alternatively, at step seven the sample could then be immediately analyzed utilizing a centralized lab or point of care assay.

A preferred absorbent material includes, but is not limited to a sponge, foam, gauze, felt, or cloth. The absorbent material is biocompatible and can be made out of natural or synthetic materials. Natural materials include, but are not limited to, cotton. Synthetic materials include, but are limited to, polymers such as nylon.

2. Methods of Obtaining Samples from Joints

Any number of methods known in the art can be used to obtain joint samples for the detection of fibronectin-aggrecan complexes. Suitable methods include, but are not limited to, percutaneous or open aspiration, biopsy, or lavage.

3. Methods for Detecting Fibronectin-Aggrecan Complexes

Any known method for detecting the presence of polypeptides in a biological sample may be used to qualitatively or quantitatively detect the presence of fibronectin-aggrecan complexes in spinal or joint samples. Suitable methods include, but are not limited to, chromatographic methods, selective binding assays, mass spectrometry, spectrophotometry, or combinations thereof.

Exemplary binding assays include immunoassays, such as enzyme-linked immunosorbent assays. Immunoassays can be used to qualitatively or quantitatively analyze a spinal sample for the presence of fibronectin-aggrecan complexes. A general overview of the applicable technology can be found in a number of readily available manuals, e.g., Harlow & Lane, Cold Spring Harbor Laboratory Press, Using Antibodies: A Laboratory Manual (1999).

a. Selective Binding Partners

In some embodiments, the disclosed methods and kits utilize selective binding partners of fibronectin or aggrecan to identify their presence or determine their levels in samples from the spine or joint. The selective binding partners may be antibodies, or other biomolecules that specifically bind to either fibronectin or aggrecan, or fragments or complexes thereof.

In some embodiments, monoclonal or polyclonal antibodies are used. The antibodies may be any known in the art, including commercially available antibodies. It is well known to those of skill in the art that the type, source and other aspects of an antibody to be used is a consideration to be made in light of the assay in which the antibody is used. In some instances, antibodies that will recognize its antigen target (for instance, an epitope or multiple epitopes from fibronectin or aggrecan) on a Western blot might not be applicable to all ELISA or ELISpot assay and vice versa.

In some embodiments, the antibodies, antibody fragments, or single chain antibodies to be used can be produced using techniques for producing monoclonal or polyclonal antibodies that are well known in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495-497

(1975). Such techniques include antibody preparation by selection of antibodies from libraries of recombinant antibodies in phage or similar vectors, as well as preparation of polyclonal and monoclonal antibodies by immunizing rabbits or mice (see, e.g. Huse et al., Science 246:1275-1281 (1989); Ward et al., Nature 341:544-546 (1989)).

A number of immunogens from fibronectin or from aggrecan may be used to produce antibodies specifically reactive with fibronectin and aggrecan and fragments thereof. For example, recombinant fibronectin or aggrecan or an antigenic fragment thereof, can be isolated using methods well known to those of skill in the art. Recombinant protein can be expressed in eukaryotic or prokaryotic cells. Recombinant protein is the typically used immunogen for the production of monoclonal or polyclonal antibodies. Alternatively, synthetic peptides derived from the known sequences of fibronectin and aggrecan and conjugated to a carrier protein can be used as an immunogen. Naturally-occurring protein may also be used either in pure or impure form. The product is then injected into an animal capable of producing antibodies. Either monoclonal or polyclonal antibodies may be generated, for subsequent use in immunoassays to measure the protein.

In other embodiments, antibodies that specifically bind to complexes containing fibronectin and aggrecan are used as specific binding partners. In certain embodiments, antibodies that specifically bind to antigens present in fibronectin-aggrecan complexes, but not when either fibronectin or aggrecan alone, are used.

In other embodiments, non-antibody polypeptides are used as specific binding agents for the detection of fibronectin or aggrecan, or fragments or complexes thereof. A large number of proteins that specifically bind to fibronectin are known in the art. Exemplary proteins that may be used as selective binding partners of fibronectin include, but are not limited to, cell-surface integrins, collagen, fibrin, lectin and heparin sulfate. Polypeptides that may be used as selective binding partners of aggrecan include, but are not limited to, tenascin-R, tenascin-C, fibulin-1, fibulin-2 and fibrillin-1.

b. Assays

Once selective binding partners are available, each specific biomarker can be detected by a variety of selective binding assays, including immunoassay methods. For a review of immunological and immunoassay procedures, see Basic and Clinical Immunology (Stites & Terr eds., 7th ed. 1991). Moreover, the disclosed selective binding assays can be performed in any of several configurations. Several immunoassay configurations are reviewed extensively in Enzyme Immunoassay (Maggio, ed., 1980).

Certain embodiments provide methods for detecting the presence and/or measuring a level of fibronectin-aggrecan in a spinal or joint sample, using specific binding partners of fibronectin or aggrecan, or fragments or complexes thereof. The methods generally include:

a) contacting the spinal or joint sample with specific binding partner for fibronectin or aggrecan, or fragments or complexes thereof; and b) detecting binding between the specific binding partner and molecules of the sample.

Detection of specific binding of the specific binding partners with molecules of the sample, when compared to a suitable control, is an indication that biomarkers are present in the sample. A variety of methods to detect specific protein interactions are known in the art and can be used in the method. Methods include competitive assays and noncompetitive assays.

Suitable methods include, but are not limited to, Western blot, immunoprecipitation, ELISA and radioimmunoassays. Methods for performing these and other suitable assays are known in the art. In general, the specific binding partner used to detect the biomarker will be delectably labeled, either directly or indirectly. The spinal or joint sample may be brought into contact with and immobilized on a solid support or carrier, such as a membrane (i.e. nitrocellulose) or polystyrene or magnetic beads, that is capable of immobilizing cells, cell particles, or soluble proteins. The support may then be washed with suitable buffers, followed by contacting with a detectably-labeled selective binding partner.

Preferred methods include those that selectively detect complexes containing fibronectin and aggrecan polypeptides or fragments thereof as compared to fibronectin and/or aggrecan that is not in a fibronectin-aggrecan complex. Suitable binding assays for such selective detection of fibronectin-aggrecan complexes include assays that use selective binding partners that bind to fibronectin-aggrecan complexes and do not detect fibronectin and/or aggrecan that is not present in such a complex. Suitable selective binding partners for use in these assays include antibodies that recognize epitopes that are present in fibronectin-aggrecan complexes, but are not present in either fibronectin or aggrecan that is not in a fibronectin-aggrecan complex. Epitopes that are specific to fibronectin-aggrecan complexes as compared to non-complexed fibronectin or aggrecan may be partially formed of amino acid sequences from each of these polypeptides. In this way, each polypeptide makes a contribution to the epitope. Epitopes that are specific to fibronectin-aggrecan complexes as compared to non-complexed fibronectin or aggrecan may also be present due to conformational differences in these polypeptides in complexes that cause epitopes that are normally "masked" to become accessible to binding by antibodies or other polypeptides.

Other suitable assays include those that use specific binding partners for each of fibronectin and aggrecan in combination to detect fibronectin-aggrecan complexes. Co-immunoprecipitation and heterogenous ELISA assays are exemplary of these types of assays. In these assays, a first specific binding partner for a first polypeptide is used to "capture" the complex, and a second selective binding partner for a second polypeptide is used to detect the complex. Methods for detecting polypeptide complexes by heterogeneous ELISA and by co-immunoprecipitation followed by Western blotting are well known in the art. The examples below demonstrate the use of a heterogeneous ELISA system using anti-fibronectin and anti-aggrecan antibodies to detect fibronectin-aggrecan complexes in human samples.

In all specific binding assays, it is desirable to minimize the amount of non-specific binding that occurs, particularly when the specific binding partner is attached to a substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used. In addition to, or in place of proteinaceous material, various detergents and/or salt can be incorporated into the immunoassay to minimize non-specific interactions. Throughout the assays, incubation and/or washing steps may be required after each combination of reagents. Incubation and washing times will depend upon several factors, including the assay format, the affinity of the specific binding partner for the biomarker, the volume of solution, concentrations.

One embodiment provides a positive control for fibronectin-aggrecan complexes that can be used in the detection assays, for example to calibrate the detection assay. In certain embodiments, fibronectin and aggrecan are from different sources, for example from different species. The fibronectin can be human fibronectin and the aggrecan can be bovine, porcine, or equine aggrecan. Alternatively, fibronectin can be bovine, porcine, or equine and aggrecan can be human. It will be appreciated that any combination can be used provided the fibronectin and aggrecan are from the same or different species with sequence homology to human sequences. The fibronectin and aggrecan can be recombinant, natural or a combination thereof.

c. Detectable Labels

Specific binding assays, including immunoassays, often use a labeling agent to specifically bind to and allow for the detection of the complex formed by the specific binding partner and the detected analyte. The labeling agent may be a part of the specific binding partner used to detect the analyte. Alternatively, the labeling agent may be a third moiety, such as a secondary antibody, which specifically binds to the complex formed by the specific binding partner and the detected analyte. Other proteins capable of specifically binding immunoglobulin constant regions, such as protein A or protein G, may also be used as the label agent. These proteins exhibit a strong affinity for immunoglobulin constant regions from a variety of species (see, e.g. Kronval et al., J. Immunol. 111: 1401-1406 (1973); Akerstrom et al., J. Immunol. 135:2589-2542 (1985)). The labeling agent can be modified with a detectable moiety, such as biotin, to which another molecule can specifically bind, such as streptavidin. A variety of detectable moieties are well-known to those skilled in the art.

The detectable label may be any material having a detectable physical or chemical property. Many useful detectable labels are known in the art and include any label that is detectable by spectroscopic, photochemical, biochemical, immunochemical, radiographic, electrical, optical or chemical means. The choice of label may depend on the sensitivity required, the ease of conjugation with the compound, stability requirements, available instrumentation, and disposal provisions. Useful labels include magnetic beads (e.g., DYNABEADS®), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and calorimetric labels such as colloidal gold or colored glass or plastic beads (e.g., polystyrene, polypropylene, latex, etc.).

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the biomarkers, or secondary antibodies that recognize the antibodies to the biomarkers.

The molecules can also be conjugated directly to signal generating compounds, for example, by conjugation with an enzyme or fluorophore. Enzymes that may be used as labels will primarily be hydrolases, particularly phosphatases, esterases and glycosidases, or oxidotases, particularly peroxidases. Exemplary fluorescent compounds include, but are not limited to, fluorescein and its derivatives, rhodamine and its derivatives, dansyl and umbelliferone. Exemplary chemiluminescent compounds include, but are not limited to, luciferin and 2,3-dihydrophthalazinediones. Means of detecting labels are well known to those of skill in the art.

E. Diagnosis and Prognosis

Methods for detecting fibronectin-aggrecan complexes to identify sites in the spine or joint that are a source of pain may be used to diagnose, or assist in the diagnosis of, subjects with pain syndromes related to the anatomic structure and physiologic function of the spine or joint.

1. Diagnosis and Prognosis of Spinal-Pain

For example, the identification of fibronectin-aggrecan complexes in the epidural space, intervertebral disk, or facet joint may be used to diagnose, or assist in the diagnosis of radiculopathy, facet joint pain or discogenic pain.

The amount of fibronectin-aggrecan complexes that will indicate a specific location in the spine as a source of pain for a particular subject will depend on numerous factors, including, but not limited to, the age, sex, medical history, etc., of the patient, the site that the biological sample was extracted from, and the assay format used to detect the biomarker. In some embodiments, the level of fibronectin-aggrecan complexes in a biological sample will not be quantified or directly compared with a control sample, but will rather be detected relative to a "diagnostic presence" of fibronectin-aggrecan complexes wherein a "diagnostic presence" refers to an amount of fibronectin-aggrecan complexes that indicates the presence or likelihood of the presence of a pain-causing pathology or injury at the location from which the sample was taken. In some embodiments, a "diagnostic presence" will be detectable in a simple assay giving a positive or negative result, where a positive "detection" of a "diagnostic presence" of fibronectin-aggrecan complexes indicates the presence of a pain-causing pathology or injury at the location from which the sample was taken.

The level of fibronectin-aggrecan complexes need not be quantified for a "diagnostic presence" to be detected. Rather, any method of determining whether fibronectin-aggrecan complexes are present at levels higher than in a normal or control may be used. In addition, a "diagnostic presence" does not refer to any absolute quantity of fibronectin-aggrecan complexes, but rather to an amount that, depending on the biological sample, assay conditions, medical condition of the patient, etc., is sufficient to distinguish the level in an affected patient from a normal or control patient.

The disclosed methods may be used regardless of whether fibronectin-aggrecan complexes are normally present, or expected to be present, in a particular control sample. For example, fibronectin-aggrecan complexes may not be detectable in certain normal spine samples (such as, for example, in a disk space or epidural space lavasate) using a particular assay, resulting in a complete absence of fibronectin-aggrecan complexes in a control biological sample. For such biological samples, a "diagnostic presence" refers to any detectable amount of fibronectin-aggrecan complexes using that same assay. In other instances, however, there may be a detectable level of fibronectin-aggrecan complexes present in normal or control samples and a "diagnostic presence" represents a level that is higher than the normal level, preferably representing a statistically significant increase over the normal level. In some embodiments, a "diagnostic presence" of fibronectin-aggrecan complexes in a biological sample will be at least about 1, 5, 2, 5, 10, 100, 200, 500, 1000 or more fold greater than a control sample. Control samples may be samples that are taken from an individual or a group of individuals not experiencing spinal pain. Alternatively, control samples may be obtained from a level of the spine not suspected to be a source of pain. For example, in a subject experiencing discogenic pain, the control sample may be obtained from an unaffected or asymptomatic disk space of the same patient.

The presence or level of fibronectin-aggrecan complexes present at a particular level within the spine can be used to diagnose, or assist in the diagnosis of, a particular type of spinal pain, such as discogenic, facetogenic or radiculopathic pain. Additionally, or alternatively, the presence or level of fibronectin-aggrecan complexes in a spinal sample can be used to distinguish pain that results from spinal pathology or injury from pain originating from another source, such as muscular pain.

In some embodiments, the presence or level of fibronectin-aggrecan complexes at a particular location along the spine is indicative of pathology or injury at that particular location. For example, if fibronectin-aggrecan complexes are detected in the L5 disc lavasate, the patient has an injury or pathology at L5. The presence of fibronectin-aggrecan complexes can then be used to diagnose injury and administer treatment at a particular location irrespective of whether injury was detectable by other methods, e.g., an MRI. The patient will typically be treated by administration of a therapeutic agent to the site of injury or pathology, i.e., the site of presence of fibronectin-aggrecan complexes.

The presence or level of fibronectin-aggrecan complexes in a biological sample can be used to designate a patient as candidate for a particular treatment. A spinal sample obtained from the patient is analyzed for the presence or absence of fibronectin-aggrecan complexes. The patient is selected for treatment if fibronectin-aggrecan complexes are detected in the spinal sample. The type of treatment, e.g., anti-inflammatory agent or surgery, can be then tailored to the severity of the condition as determined by the presence or level of fibronectin-aggrecan complexes.

The level of fibronectin-aggrecan complexes present at a specific site may also be useful to determine a prognosis for the subject being tested. For example, the level of fibronectin-aggrecan complexes present in a spinal sample may indicate the extent of an acute injury to the spine and can assist a practitioner in determining to what extent successful repair or healing of the injury or pathology can be achieved.

2. Diagnosis and Prognosis of Joint Pain

Methods for detecting fibronectin-aggrecan complexes to identify joints as sites for treating joint-related pain may be used to diagnose, or assist in the diagnosis of, subjects with pain syndromes related to the anatomic structure and physiologic function of the synovial joints of the appendicular skeleton. For example, the identification of fibronectin-aggrecan complexes in a joint may be used to diagnose, or assist in the diagnosis of osteoarthritis, meniscal pathology, rotator cuff tears, tendon or ligament pathology, chondroisis, or myofascial pain.

The amount of fibronectin-aggrecan complexes that will indicate a joint as a site for treating joint-related pain for a particular subject will depend on numerous factors, including, but not limited to, the age, sex, medical history, etc., of the patient, the site that the biological sample was extracted from, and the assay format used to detect the biomarker. In some embodiments, the level of fibronectin-aggrecan complexes in a biological sample will not be quantified or directly compared with a control sample, but will rather be detected relative to a "diagnostic presence" of fibronectin-aggrecan complexes wherein a "diagnostic presence" refers to an amount of fibronectin-aggrecan complexes that indicates the presence or likelihood of the presence of a pain-causing pathology or injury at the location from which the sample was taken. In some embodiments, a "diagnostic presence" will be detectable in a simple assay giving a positive or negative result, where a positive "detection" of a "diagnostic presence" of fibronectin-aggrecan complexes indicates the presence of a pain-causing pathology or injury at the location from which the sample was taken.

The level of fibronectin-aggrecan complexes need not be quantified for a "diagnostic presence" to be detected. Rather, any method of determining whether fibronectin-aggrecan complexes are present at levels higher than in a normal or control may be used. In addition, a "diagnostic presence" does not refer to any absolute quantity of fibronectin-aggrecan complexes, but rather to an amount that, depending on the biological sample, assay conditions, medical condition of the patient, etc., is sufficient to distinguish the level in an affected patient from a normal or control patient.

The disclosed methods may be used regardless of whether fibronectin-aggrecan complexes are normally present, or expected to be present, in a particular control sample. For example, fibronectin-aggrecan complexes may not be detectable in certain normal joint samples (such as, for example, in a synovial fluid sample) using a particular assay, resulting in a complete absence of fibronectin-aggrecan complexes in a control biological sample. For such biological samples, a "diagnostic presence" refers to any detectable amount of fibronectin-aggrecan complexes using that same assay. In other instances, however, there may be a detectable level of fibronectin-aggrecan complexes present in normal or control samples and a "diagnostic presence" represents a level that is higher than the normal level, preferably representing a statistically significant increase over the normal level. In some embodiments, a "diagnostic presence" of fibronectin-aggrecan complexes in a biological sample will be at least about 1.5, 2, 5, 10, 100, 200, 500, 1000 or more fold greater than a control sample. Control samples may be samples that are taken from an individual or a group of individuals not experiencing joint-related pain. Alternatively, control samples may be obtained from unaffected or asymptomatic joints from the subject being tested. Particularly suitable joints to obtain control samples from are joints that are unaffected or asymptomatic contra-lateral to the joint being tested for a diagnostic presence of fibronectin-aggrecan complexes. For example, in a subject experiencing left knee pain, the control sample may be obtained from the right knee of the same subject, provided that the right knee is unaffected or asymptomatic.

The presence or level of fibronectin-aggrecan complexes present in a particular joint can be used to diagnose, or assist in the diagnosis of, a particular type of joint-related pain, including, but not limited to, osteoarthritis, meniscal pathology, rotator cuff tears, tendon or ligament pathology, chondroisis, or myofascial pain. In some embodiments, the presence or level of fibronectin-aggrecan complexes in a joint is indicative of pathology or injury in that particular joint. Additionally, or alternatively, the presence or level of fibronectin-aggrecan complexes in a joint sample can be used to distinguish joint-related pain from pain from another anatomical or physiological source, such as the spine. For example, the presence or increased level of fibronectin-aggrecan complexes in a joint sample compared to a control sample may be used to distinguish joint-related pain from radiculopathic pain.

Detection of fibronectin-aggrecan complexes can be used alone, or in combination with other diagnostic approaches to diagnose joint-related pain. Exemplary diagnostic approaches include, but are not limited to, medical history and physical examination, x-ray radiography, MRI and intra-articular injection. The presence of fibronectin-aggrecan complexes may however be used to diagnose injury and administer treatment at a particular location irrespective of whether injury was detectable by other methods, e.g., an MRI. The patient will typically be treated by administration of a therapeutic agent to the site of injury or pathology, i.e., the site of presence of fibronectin-aggrecan complexes.

The presence or level of fibronectin-aggrecan complexes in a biological sample can be used to designate a patient as candidate for a particular treatment. The type of treatment, e.g., administration of an anti-inflammatory agent or surgery, can be then tailored to the severity of the condition as determined by the presence or level of fibronectin-aggrecan complexes.

The level of fibronectin-aggrecan complexes present at a specific site may also be useful to determine a prognosis for the subject being tested. For example, the level of fibronectin-aggrecan complexes present in a joint sample may indicate the extent of an acute injury to the joint and can assist a practitioner in determining to what extent successful repair or healing of the injury or pathology can be achieved.

D. Monitoring the Efficacy of Treatment

The disclosed methods may also be used to assess the efficacy of a treatment or a course of treatment. For example, in a patient with radiculopathy testing positive for a "diagnostic presence" of fibronectin-aggrecan complexes indicative or radiculopathy, the efficacy of an anti-inflammatory treatment can be assessed by monitoring, over time, the levels of fibronectin-aggrecan complexes. A reduction in the levels of fibronectin-aggrecan complexes in a biological sample taken from a patient following a treatment, compared to a level in a sample taken from the same patient before, or earlier in, the treatment, indicates efficacious treatment.

In a patient with joint-related pain testing positive for a "diagnostic presence" of fibronectin-aggrecan complexes in a joint sample, the efficacy of an anti-inflammatory treatment can be assessed by monitoring, over time, the levels of fibronectin-aggrecan complexes in the treated joint. For example, a reduction in the levels of fibronectin-aggrecan complexes in a biological sample taken from a patient following a treatment, compared to a level in a sample taken from the subject before, or earlier in, the treatment, indicates efficacious treatment.

IV. Methods for Treating Pain

Once the site from which the pain is originating is identified by the presence of fibronectin-aggrecan complexes, any method known in the art may be used to treat the pain, or to treat the pathology that is causing the pain. For example, if radiculopathy or discogenic pain or facet pain has been diagnosed, any number of methods known in the art for treating spinal pain can be applied to treat the patient. Suitable methods include, but are not limited to, laminotomy, laminectomy, discectomy, microdiscectomy, percutaneous discectomy, endoscopic discectomy, laser discectomy, foramenotomy, fusion, prolotherapy, other surgical decompressions, decompression with fusion with or without instrumentation.

Pain in the spine may also be treated by standard nonsurgical methods, including administration of steroidal or non-steroidal anti-inflammatory agents. Non-steroidal anti-inflammatory (NSAID) agents are well known in the art. Non-steroidal agents, including NSAIDs such as ibuprofen, aspirin or paraceramol may be used. Steroids, such as glucocorticoids, which reduce inflammation by binding to cortisol receptors, may also be used for treatment.

Any number of methods known in the art for treating joint-related pain can be applied to treat the patient. Suitable methods include surgical and non-surgical methods including, but not limited to, arthroscopic debridement or administration of steroidal or non-steroidal anti-inflammatory agents.

A. Biomarker Antagonists

In some embodiments, one or more antagonists of fibronectin-aggrecan complexes may be used to treat spinal or joint pain. Suitable fibronectin-aggrecan complex antagonists may directly or indirectly inhibit or reduce the biological activity of fibronectin-aggrecan complexes. Other suitable fibronectin-aggrecan complex antagonists inhibit or reduce the formation of complexes of fibronectin and aggrecan from fibronectin and aggrecan monomers or cause the dissociation of existing complexes containing fibronectin and aggrecan. Still other suitable fibronectin-aggrecan complex antagonists inhibit or reduce the expression of fibronectin or aggrecan.

1. Antibodies

In one embodiment, fibronectin-aggrecan complex antagonists are antibodies. Antibodies or antibody fragments that specifically bind to fibronectin or aggrecan can be used to inhibit or reduce the formation of fibronectin-aggrecan complexes, to dissociate existing fibronectin-aggrecan complexes and/or to inhibit or reduce the biological activity of fibronectin-aggrecan complexes. Methods of producing antibodies are well known and within the ability of one of ordinary skill in the art and are described in more detail below.

The antibodies disclosed herein specifically bind to a fibronectin or an aggrecan polypeptide, or a fragment thereof, and are capable of reducing or inhibiting the binding of fibronectin to aggrecan, or the binding of fibronectin-aggrecan complexes to biological targets that mediate signaling resulting in pain. Other suitable antibodies specifically bind to fibronectin-aggrecan complexes, rather than either of these polypeptides individually. These antibodies are particularly useful, because they do not interfere with functions of fibronectin and aggrecan outside of their functions in a complex.

The disclosed antibodies are defined as "blocking", "function-blocking" or "antagonistic" antibodies. The immunogen used to generate the antibody may be any immunogenic portion of fibronectin or aggrecan. In one embodiment, the immunogen used to generate anti-aggrecan antibodies is the G3 domain of aggrecan. Immunogens are produced in a variety of ways known in the art, e.g., expression of cloned genes using conventional recombinant methods, synthesized peptide complexes, isolation from cells of origin, cell populations expressing high levels of fibronectin or aggrecan. In another embodiment, the immunogen contains fibronectin-aggrecan complexes. The complexes may be isolated from biological samples from a subject or may be produced by formation of complexes in vitro from fibronectin and aggrecan monomers.

The antibodies may be polyclonal or monoclonal antibodies. The antibodies may be xenogeneic, allogeneic, syngeneic, or modified forms thereof, such as humanized or chimeric antibodies. The antibodies may also be antiidiotypic antibodies. Antibodies, as used herein, also includes antibody fragments including Fab and F(ab)$_2$ fragments, and antibodies produced as a single chain antibody or scFv instead of the normal multimeric structure. The antibodies may be an IgG such as IgG1, IgG2, IgG3 or IgG4; or IgM, IgA, IgE or IgD isotype. The constant domain of the antibody heavy chain maybe selected depending on the effector function desired. The light chain constant domain may be a kappa or lambda constant domain.

Commercially available or other antibodies known in the art that bind to fibronectin or aggrecan may be used. For example, humanized antibodies that bind to fibronectin are described in U.S. Pat. Nos. 6,329,511 and 7,183,390.

2. Other Polypeptides

In another embodiment, biomarker antagonists are polypeptides other than antibodies that bind to fibronectin or aggrecan, or complexes thereof. Fibronectin- or aggrecan-binding polypeptides can be used to reduce or inhibit the formation of complexes containing fibronectin and aggrecan and/or to inhibit or reduce the biological activity of fibronectin-aggrecan complexes. Methods of producing polypeptides are well known in the art.

In some embodiments the polypeptides are soluble fragments of fibronectin or aggrecan receptors. Exemplary fibronectin receptors include fibronectin receptors 1 and 2. Other suitable soluble polypeptides include viral proteins known to bind to fibronectin or aggrecan. For example, chimeric viroreceptors which bind to various species of fibronectin may be used.

3. Small Molecules and Other Antagonists

It will be appreciated that additional bioactive agents may be screened for antagonistic activity. In one embodiment, candidate bioactive agents are screened for their ability to inhibit or reduce the formation of complexes containing fibronectin and aggrecan or to dissociate existing complexes. In another embodiment, candidate bioactive agents are screened for their ability to reduce the binding of complexes of fibronectin and aggrecan to biological targets or for their ability to inhibit or reduce biological activities of fibronectin-aggrecan complexes.

The term "candidate bioactive agent" as used herein describes any molecule, e.g., protein, small organic molecule, small inorganic molecule, organo-metallic molecules, carbohydrates (including polysaccharides), polynucleotide, lipids, etc. Generally a plurality of assay mixtures is run in parallel with different agent concentrations to obtain a differential response to the various concentrations. Typically, one of these concentrations serves as a negative control, i.e., at zero concentration or below the level of detection. In addition, positive controls, i.e. the use of agents known to bind fibronectin or aggrecan may be used.

Candidate agents include organic, inorganic, organo-metallic, synthetic, semi-synthetic and naturally occurring small molecules. Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides, e.g., peptidomimetics. Peptidomimetics can be made as described, e.g., in WO 98156401.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs. In a preferred embodiment, the candidate bioactive agents are organic chemical moieties or small molecule chemical compositions, a wide variety of which are available in the art.

4. Antagonists that Reduce or Inhibit the Expression of Fibronectin or Aggrecan In another embodiment, antagonists reduce or inhibit the expression of fibronectin or aggrecan. Antagonists that reduce or inhibit expression of fibronectin or aggrecan include inhibitory nucleic acids, including, but not limited to, ribozymes, triplex-forming oligonucleotides (TFOs), antisense DNA, siRNA, and microRNA specific for nucleic acids encoding fibronectin or aggrecan.

Useful inhibitory nucleic acids include those that reduce the expression of RNA encoding fibronectin or aggrecan by at least 20%, 30%, 40%, 50%, 60%, 70%, 80%, 90% or 95% compared to controls. Expression of fibronectin or aggrecan can be measured by methods well know to those of skill in the art, including northern blotting and quantitative polymerase chain reaction (PCR).

Inhibitory nucleic acids and methods of producing them are well known in the art. siRNA design software is available for example at http://i.cs.hku.hk/~sirna/software/sirna.php. Synthesis of nucleic acids is well known see for example Molecular Cloning: A Laboratory Manual (Sambrook and Russel eds. $3^{rd}$ ed.) Cold Spring Harbor, N.Y. (2001). The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. The double-stranded RNA portions of siRNAs in which two RNA strands pair up are not limited to the completely paired ones, and may contain nonpairing portions due to mismatch (the corresponding nucleotides are not complementary), and bulge (lacking in the corresponding complementary nucleotide on one strand). Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the siRNA is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

miRNAs are produced by the cleavage of short stem-loop precursors by Dicer-like enzymes; whereas, siRNAs are produced by the cleavage of long double-stranded RNA molecules. miRNAs are single-stranded, whereas siRNAs are double-stranded.

Methods for producing siRNA are known in the art. Because the sequences for fibronectin or aggrecan known, one of skill in the art could readily produce siRNAs that downregulate fibronectin or aggrecan expression using information that is publicly available.

5. Inhibitors of Aggrecanases And Matrix Metaloproteases (MMP's) Responsible for Fibronectin and/or Aggrecan Degradation In one embodiment, known inhibitors such as chelators of known aggrecanases or MMP's can be administered to a subject in need thereof in amount effective to inhibit or slow down the release of aggrecan fragments which in effect will reduce or eliminate the formation of the fibronectin aggrecan complexes thereby giving relief to the subject from the pain.

B. Pharmaceutical Compositions

Pharmaceutical compositions including fibronectin-aggrecan complex antagonists are provided. Pharmaceutical compositions containing peptides or polypeptides may be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The compositions may also be administered using bioerodible inserts and may be delivered directly to spinal structures, such as intervertebral discs, the epidural space and facet joints, or to diarthoidal joints. The compositions can be formulated in dosage forms appropriate for each route of administration. Compositions containing fibronectin-aggrecan complex antagonists that are not peptides or polypeptides can additionally be formulated for enteral administration.

The antagonists disclosed herein are administered to a subject in a therapeutically effective amount. As used herein the term "effective amount" or "therapeutically effective amount" means a dosage sufficient to treat, inhibit, or alleviate spinal pain in a subject in need thereof. The precise dosage will vary according to a variety of factors such as subject-dependent variables (e.g., age, etc.), the injury or pathology being treated, and the treatment being effected. For the fibronectin-aggrecan complex antagonists disclosed herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the route of administration, and on the duration of the treatment desired. Generally dosage levels of 0.001 to 10 mg/kg of body weight daily are administered to mammals. Generally, for intravenous injection or infusion, dosages may be lower.

In one embodiment, fibronectin-aggrecan complex antagonists, including those containing peptides and polypeptides, are administered in an aqueous solution by parenteral, intradiscal, intrafacet, intrathecal, epidural or joint injection. In preferred embodiments, fibronectin-aggrecan complex antagonists are administered directly into the area of the spine that is the source of pain in the subject. For example, when fibronectin-aggrecan complexes are detected in the epidural space, fibronectin-aggrecan complex antagonists may be administered by direct injection into the epidural space. Alternatively, fibronectin-aggrecan complex antagonists may be administered by direct injection into the disc space, facet joint, or diarthoidal joint when fibronectin-aggrecan complexes are detected in these spaces.

The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Fibronectin-aggrecan complex antagonists, including those containing peptides and polypeptides, may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fibronectin-aggrecan complex antagonists, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

V. Kits

Detection methods employing specific binding assays, such as immunoassays, are particularly suitable for practice at the point of patient care. Such methods allow for immediate diagnosis and/or prognostic evaluation of the patient.

Kits for use in diagnostic, research, and therapeutic applications described above are also provided. In the diagnostic and research applications such kits may include any or all of the following: assay reagents, buffers, and selective binding partners for the disclosed biomarkers all of which can be housed in a container suitable for transport. The selective binding partners may include antibodies that selectively bind to fibronectin-aggrecan complexes, or that bind to each of these components individually for use in combination. In some embodiments, the kits include the selective binding partners on a continuous solid surface.

An exemplary kit includes a container having a detection binding partner and a positive control for detecting fibronectin-aggrecan complexes. The positive control can be fibronectin-aggrecan complexes or the components for making fibronectin-aggrecan complexes. Fibronectin and aggrecan sequences could be human sequences or any other species where the aggrecan and fibronectin are homologous to human sequences. Both fibronectin and aggrecan can originate from the same species or different species. The fibronectin and/or aggrecan fragment can be purified from natural sources or synthesized by solid phase methods or produced by recombinant methods. The kit can also include a capture binding partner bound to a substrate such as the continuous solid surface. The capture binding partner typically binds aggrecan in a fibronectin-aggrecan complex and the detection binding partner binds fibronectin in the fibronectin-aggrecan complex, but it will be appreciated that capture binding partner can bind fibronectin and the detection binding partner can bind aggrecan.

In some embodiments, a device to be utilized for the extraction of the biological sample is also included in the kit. In some embodiments, the extraction device, e.g., a syringe, a needle and a catheter, can directly extract the biological sample from the potentially affected disk or epidural space or joint into a chamber containing the selective binding partners for the biomarker. In some instances, the kit, thus allows for immediate assessment of the presence and/or level of the biomarker. These types of kits are particularly suitable for use at the point of care. An example of a point of care diagnostic system is described in U.S. Pat. No. 6,267,722. Other devices whose design can be adapted for use with the kits of the present invention are described, for example, in U.S. Pat. Nos. 7,198,522 and 6,818,455.

In some embodiments, the kit may include a solution to be used for the extraction of the biological sample from the spine or joint. This solution included in the kit can be, for example, a physiologic solution, e.g. saline. In some embodiments, the kit may include one or more therapeutic agents which can be administered through the same device as used for the extraction of the sample or through a different device.

In addition, the kits may include instructional materials containing directions (i.e., protocols) for the use of the materials provided in the kit. While the instructional materials typically comprise written or printed materials, they may be provided in any medium capable of storing such instructions and communicating them to an end user. Suitable media include, but are not limited to, electronic storage media (e.g., magnetic discs, tapes, cartridges, chips) and optical media (e.g., CD ROM). The media may include addresses to interne sites that provide the instructional materials.

EXAMPLES

Example 1

Application of Chromatography for the Purification of Fibronectin-Aggrecan Complexes from Human Samples To purify fibronectin-aggrecan complexes from a disc lavage sample or synovial fluid, size exclusion chromatography (SEC) followed by anion-exchange chromatography was performed. SEC and anion-exchange chromatography were carried out using the Bio-Rad BioLogic DuoFlow® computer controlled HPLC system equipped with BioLogic QuadTec® UV/VIS detector and conductivity monitor.

Figure 2:
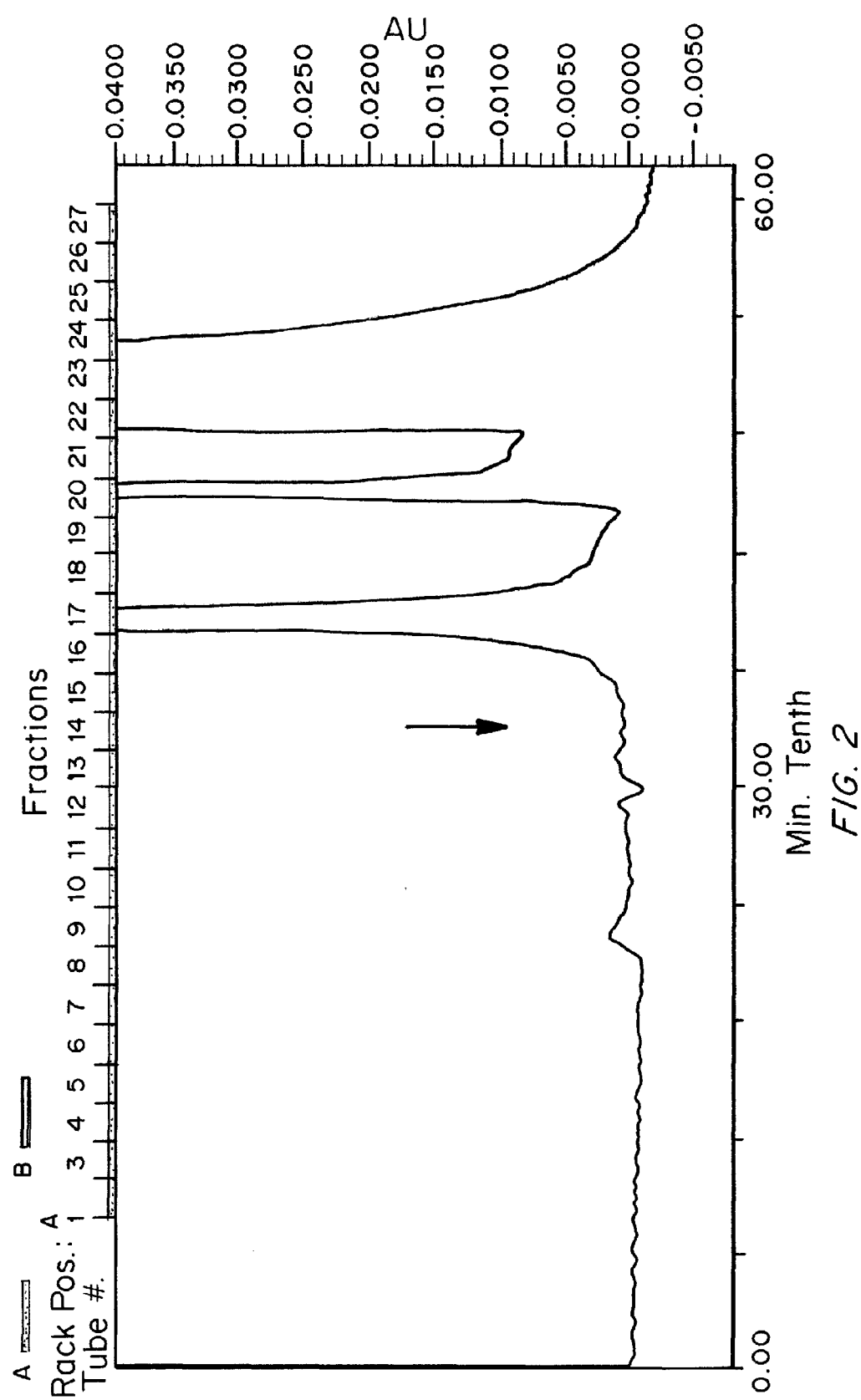
FIG. 2 is a graph showing the results of size exclusion chromatography (SEC) of an asymptomatic human sample. The graph expresses the optical density of proteins at 215 nm eluted from the SEC column as a function of elution time in minutes. The arrow identifies the location and absence of the peak where the Fibronectin/aggrecan G3 fragment detected by the assay should have been located. The other high molecular weight peaks containing complexes of fibronectin with other or bigger fragments of aggrecan were also absent.

SEC was performed using two Bio-Rad® SEC-400-5 columns in series using isocratic elution with 50 mM Tris/HCl, 100 mM NaCl, pH 8.0. The resulting fractions were analyzed for total protein content ($A_{280nm}$ and $A_{215nm}$) and for the presence of the discovered biomarker consisting of Fibronectin complexes with aggrecan fragment. FIG. 1 shows the SEC-HPLC elution profile ($A_{215nm}$) for a symptomatic sample and FIG. 2 shows the SEC-HPLC elution profile for an asymptomatic sample under the same conditions. Subsequent experimentation revealed that fractions 14 and 15 were the only fractions containing detectable levels of fibronectin-aggrecan complexes detected by the developed assay. Based on molecular weight standards for this column, proteins eluting in fractions 14 and 15 are predicted to have a molecular weight in the range of 250 Kda to 700 Kda.

Fibronectin aggrecan complex can further be purified using anion exchange chromatography. The complex was bound to the column, equilibrated with 50 mM Tris/HCl, 150 mM NaCl, pH 8.0 and eluted from the column with a linear salt gradient from 150 mM NaCl to 230 mM NaCl in Tris/HCl buffer.

Fibronectin aggrecan complex can also be purified using cation exchange chromatography. The complex was bound to the column, equilibrated with 50 mM sodium acetate, 100 mM NaCl, pH 6.0 and eluted from the column with a linear salt gradient from 100 mM NaCl to 300 mM NaCl in acetate buffer.

Example 2

Silver Stain and Western Blot Analysis Using Anti-Fibronectin, and Anti-Aggrecan (G3 Domain) Specific Antibodies Example 1 demonstrates the fractionation of a human sample by SEC-HPLC. Fractions 14 and 15 from the SEC analysis were subjected to SDS-PAGE separation followed by silver staining or Western blotting to determine the size of the proteins in the fractions and to probe their identity. Western blotting was conducted using standard methods using anti-fibronectin monoclonal (DiaPharma Group, Inc. detection antibody from DPGR028A fibronectin ELISA kit), and anti-aggrecan monoclonal (G3 domain) (Santa Cruz Biotechnology, Aggrecan C20, sc-16493) specific antibodies.

Silver staining analysis showed the presence of proteins in the range of greater than 250 Kd in both fractions. Western blotting using the anti-fibronectin monoclonal and anti-aggrecan monoclonal (G3 domain) antibodies revealed immunoreactive band at a molecular weight range of 400-600 Kd, indicating that the proteins co-migrated through the polyacrylamide gel. The data indicates the presence of a protein complex that is immunoreactive with both anti-fibronectin and anti-aggrecan (G3) antibodies.

Example 3

Analysis of Aggrecan Domains that Co-Migrate with Fibronectin Through Polyacrylamide Gels Size exclusion chromatography of a single human sample was conducted as described in Example 1 and eluted fractions 8 through 20 from the SEC were subjected to separation by SDS-PAGE and then transferred to membranes for Western blotting using polyclonal anti-aggrecan G1 (Santa Cruz Biotechnology, Aggrecan D20, se-16492), G2 (Santa Cruz Biotechnology, Aggrecan E12, se-67513) or G3 (Santa Cruz Biotechnology, Aggrecan C20, sc-16493) antibodies. Western blots using the anti-aggrecan G3 domain antibody revealed immunoreactive bands of different molecular sizes in fractions 8-20, corresponding to various proteolytic fragments of aggrecan containing the G3 domain. Western blots using the anti-aggrecan G1 domain antibody revealed immunoreactive bands in fractions 8-20 that exhibited a different banding pattern than that observed using the anti-aggrecan G3 domain antibody.

Western blots using the anti-aggrecan G2 domain antibody revealed immunoreactive bands in fractions 8-20 that exhibited a different banding pattern than that observed using either the anti-aggrecan G1 or G3 domain antibodies. Analysis of the banding patterns obtained using the anti-aggrecan G1, G2 and G3 antibodies suggests that G1, G2 and G3 domains of aggrecan, are present in different complexes with fibronectin or fragments thereof.

Example 4

Heterogeneous ELISA Analysis of Fibronectin-Aggrecan Protein Complexes

The previous examples suggest the presence of a complex of fibronectin and aggrecan (G3) in human samples. To further test for the presence of such a complex, a heterogeneous ELISA sandwich assay was developed and used.

Materials and Methods:

Size exclusion chromatography of a single human sample was conducted as described in Example 1 and fractions 14 and 15 were used for further analysis.

An anti-fibronectin monoclonal antibody (DiaPharma Group, Inc. detection antibody from DPGR028A fibronectin ELISA kit) was immobilized on a polystyrene plate to function as the capture antibody. Fractions 14 and 15 from SEC of the human sample were then aliquoted onto the plate containing the fibronectin capture antibody. Following incubation, the samples were removed, the plates were washed, and the plates were incubated with an anti-aggrecan G3 domain polyclonal antibody (Santa Cruz Biotechnology, Aggrecan C20, sc-16493) as the detection antibody. The plates were washed and the presence of complexes of fibronectin with the G3 domain of aggrecan was detected using secondary antibody labeled with HRP followed by optical detection. Additional experiments were also performed in which the anti-aggrecan G3 domain antibody was used as the capture antibody and the anti-fibronectin antibody was used as the detection antibody.

Fraction 14 demonstrates the highest optical density, with fraction 15 also positive but with lower optical density. These results demonstrate the existence of a heterogeneous complex of interacting fibronectin and aggrecan (G3 domain) in SEC fractions of a molecular weight consistent with the interacting protein complex regardless of which antibody was used to capture and which antibody was used for detection.

Example 5

Dissociation of the Fibronectin and Aggrecan (G3) Complex with Heat and a Reducing Agent As a further test for the presence of a complex containing fibronectin and the G3 domain of aggrecan, the effect of heat and a reducing agent on the migration of bands on Western blots was tested.

Materials and Methods:

Size exclusion chromatography of a single human sample was conducted as described in Example 1 and eluted fractions 14 and 15 were used for further analysis. Proteins from fractions 14 and 15 were separated on 4-20% SDS-polyacrylamide gels. The samples were either untreated, treated by heating in a boiling water bath for 3 minutes, or treated by heating in a boiling water bath for 3 minutes in the presence of the reducing agent DTT. Proteins were then transferred to membranes for Western blotting using either anti-aggrecan G3 domain monoclonal or anti-fibronectin monoclonal antibodies, as described in the examples above.

Results:

When the samples were not treated by heating or with a reducing agent, the Western blots revealed a single band immunoreactive with anti-fibronectin monoclonal antibody and anti-aggrecan (G3) monoclonal antibody.

When the samples were treated by heating in a boiling water bath for 3 minutes, subsequent Western blots revealed the splitting of single anti-fibronectin and anti-aggrecan (G3) immunopositive bands into multiple bands of lower molecular weight. This is consistent with partial dissociation of the dimeric form of fibronectin-aggrecan (G3 domain) complex into a fibronectin monomer and aggrecan (G3 domain) complex.

When the samples were treated by heating in a boiling water bath for 3 minutes in the presence of DTT, subsequent Western blots revealed the splitting of single anti-fibronectin and anti-aggrecan (G3) immunopositive bands into multiple bands of lower molecular weight. This is consistent with the dissociation of the fibronectin-aggrecan (G3 domain) complex into separate fibronectin and aggrecan (G3 domain) subunits. In addition the fibronectin was cleaved to several peptides that were held together with disulfide bonds.

This example demonstrates that gel migration characteristics of the bands positive for fibronectin and aggrecan (G3 domain) can be affected by heat and reduction, consistent with dissociation of a protein-protein complex.

Example 6

Examination of Fibronectin-Aggrecan (G3) Complex as a Biomarker for Pain in the Human Intervertebral Disc A 45-year old female diagnosed with lumbar herniated nucleus pulposus (HNP) by clinical and radiographic characteristics was further evaluated by discography. The extent of disc degeneration was determined by radiographic assessment using the Phirrmann scale. The visual analog scale (VAS) for pain was also performed for the subject, and the patient reported a VAS value of 5. VAS is a 1-10 scale, with 1 corresponding to no pain and 10 the most intense pain. Prior to the discography, the intradiscal space of the human intervertebral disc was sampled using the Disc space lavage method (Method 6). During the discography procedure, an intra-operative VAS value was obtained for each lumbar disc level. As shown in Table 1, the biomarker complex ELISA was positive in both lumbar disc levels that exhibited the most extensive radiographic measure for degeneration and also the intense intra-operative pain measurements.

TABLE 1

Characteristics at various lumbar levels of a single human volunteer with pain undergoing MRI and discography procedures.

| Age/Sex | Level | Pfirrmann | Intraop-VAS | Complex ELISA O.D. 450 nm |
|---|---|---|---|---|
| 45/F | L2-3 | 1 | 1 | 0.0 |
|  | L3-4 | 2 | 1 | 0.2 |
|  | L4-5 | 4 | 9 | 0.6 |
|  | L5-S1 | 4 | 10 | 1.0 |

Figure 4:
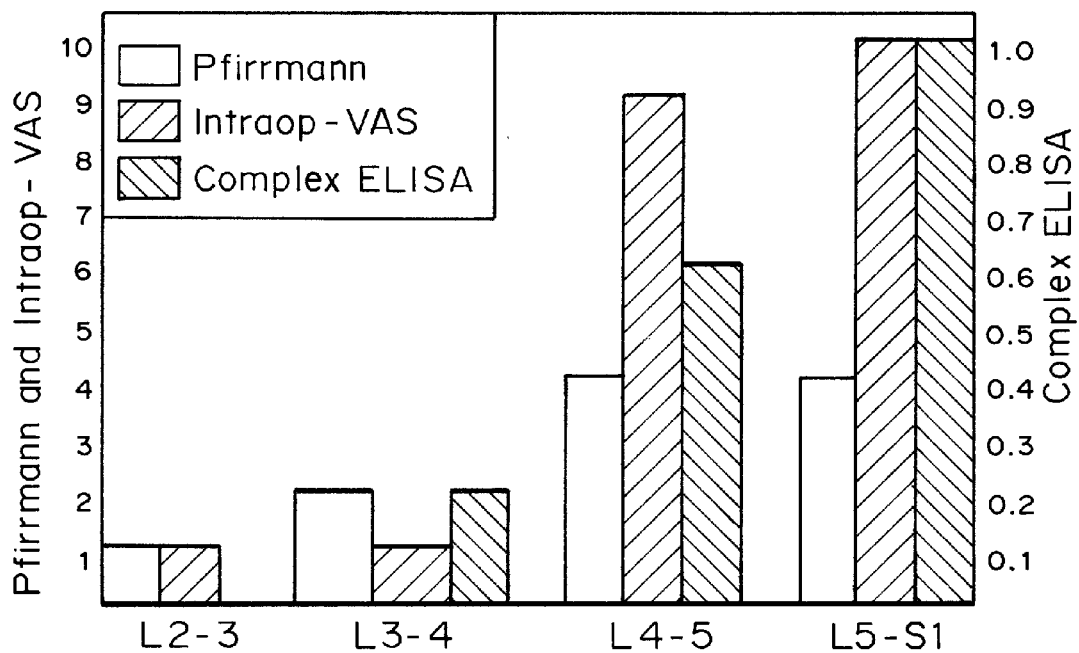
FIG. 4 is a bar graph of Pfirrmann and intra-operative VAS values from spinal samples taken from the indicated disc level analyzed by ELISA.

This example demonstrates that the presence of the fibronectin-aggrecan protein complex in the intradiscal space of the human subject correlates with clinical pain, concordant discography, and MRI. These data are presented graphically in FIG. 4.

Example 7

Positive Control for the ELISA Kit

Figure 3:
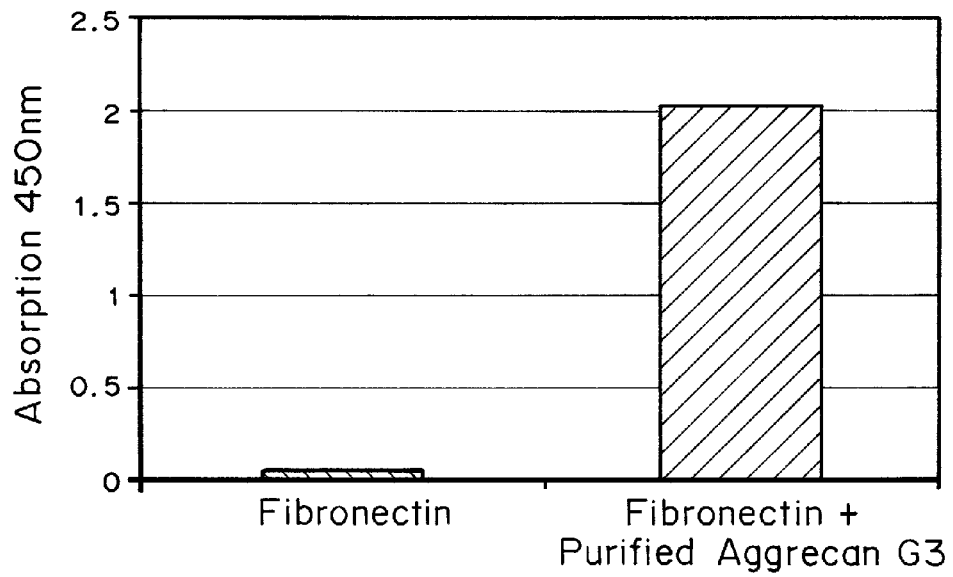
FIG. 3 is a bar graph showing the results of a negative ELISA for fibronectin and positive ELISA for fibronectin premixed with purified Bovine Aggrecan G3 fragment in vitro. Data are expressed as optical density in relative units.

In an attempt to establish a positive control for the ELISA kit, bovine aggrecan was investigated. Due to the high sequence homology of bovine aggrecan to human aggrecan, bovine aggrecan was purified from cartilage according to published methods. The purified aggrecan was then digested with MMP-9, a matrix metalloproteinase responsible for the degradation of aggrecan in vivo. The G3 and its fragments were purified via affinity chromatography with anti-aggrecan G3 domain immobilized on the Sepharose® resin. The eluted aggrecan G3 domain was mixed with human fibronectin to form the complex. The developed ELISA detected the complex assembled in vitro between human fibronectin and bovine aggrecan G3 (FIG. 3). The same principle will apply to bovine and human fibronectin which also have high homology.

Neither fibronectin or aggrecan-G3 domain alone produced a positive signal in the ELISA assay; accordingly either can be used as a negative control.

Figure 5:
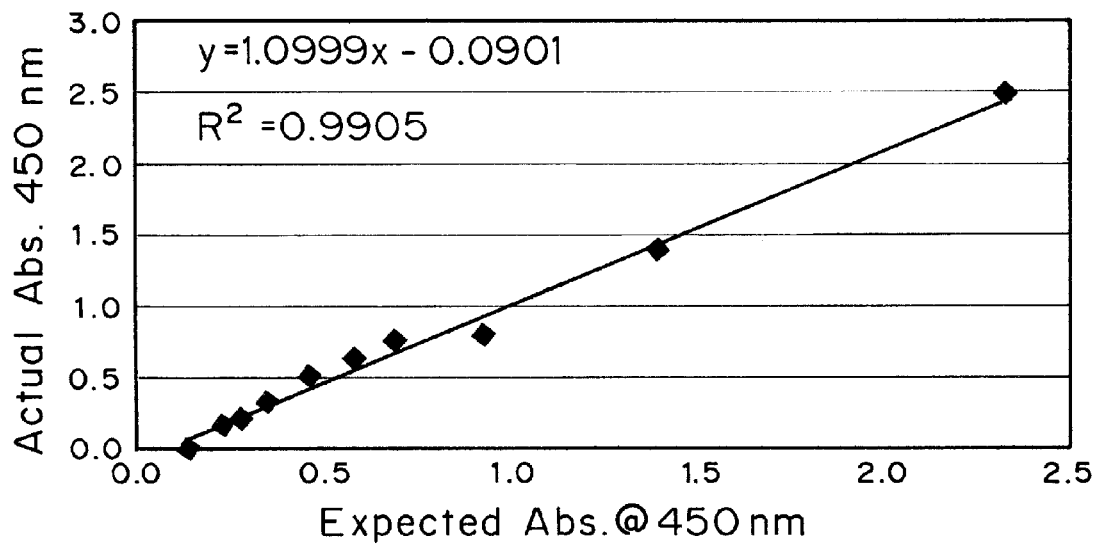
FIG. 5 is a graph showing the linearity of the ELISA using an anti-aggrecan-G3 antibody for capture and an anti-fibronectin antibody for detection. Data are expressed as actual absorbance at 450 nm versus expected absorbance at 450 nm.

FIG. 5 shows the linearity of the ELISA using an anti-aggrecan-G3 antibody for capture and an anti-fibronectin antibody for detection. A positive sample from a patient with pain was used in this experiment. The initial O.D. at 450 nm was measured by the complex ELISA. Serial dilutions of this sample were used in the linearity study. The expected O.D. was calculated from the initial measured value and the dilution factors. Under ideal conditions, this linear plot should have a slope of 1 and y intercept of 0 and $R^2=1$. The values obtained are slope=1.09 and y intercept=−0.09 with $R^2=0.99$.

It will be appreciated that the antibody for capture can be anti-fibronectin and the antibody for detection can be anti-aggrecan.

Example 8

Comparison of Synovial Fluid Samples from Painful Knees Undergoing Arthroscopic Debridement to Asymptomatic Control Knees To compare the utility of the fibronectin-aggrecan (G3) complex as a biomarker for the presence of pain in a synovial joint, the synovial fluid of painful knees in patients undergoing arthroscopy was compared to the synovial fluid of knees from asymptomatic volunteers.

Materials and Methods:

After obtaining institutional review board approval, subjects were recruited into study with a case-control series design. All subjects gave informed consent to participate. Subjects with a painful knee undergoing arthroscopic surgery were recruited from the practice of a single knee surgeon in private practice. Inclusion criteria included in the age range 30-69, activity related knee pain, failed conservative management (injections, therapy), the presence of mechanical symptoms (locking, catching, giving way), and MRI positive for meniscal tear. Exclusion criteria included the presence of high energy trauma or fracture, inflammatory arthritides, ligament injury, or oral/intra-articular steroid injection within 3 months of surgery date.

A separate set of subjects was recruited from asymptomatic volunteers without knee pain but with an age matched demographic. Inclusion criteria included age range 30-69 and the absence of knee pain or an intermittent history of knee pain. Exclusion criteria included inflammatory arthritides, oral/intra-articular steroid injection, the presence of an effusion, a history of knee surgery, or a physical examination of knee alignment and stability outside the range of normal limits.

For each subject, an intra-articular sample was collected as follows. The aspiration site was prepped with triple preparation of chlorohexidine gluconate and aspiration was performed from an anterior or direct lateral approach with a sterile 10 cc syringe and a 21 gauge×1.5 inch needle. The knee was lavaged with 10 cc of 0.9% normal saline, and then the aspirate was withdrawn into the syringe. The aspirate was aliquoted into an eppendorf tube containing protease inhibitor cocktail then placed on ice until transport.

A heterogeneous ELISA assay for the presence of fibronectin-aggrecan (G3) complex (i.e. as described in example 4) was performed on each sample after dilution in a 1:5 ratio.

Figure 6:
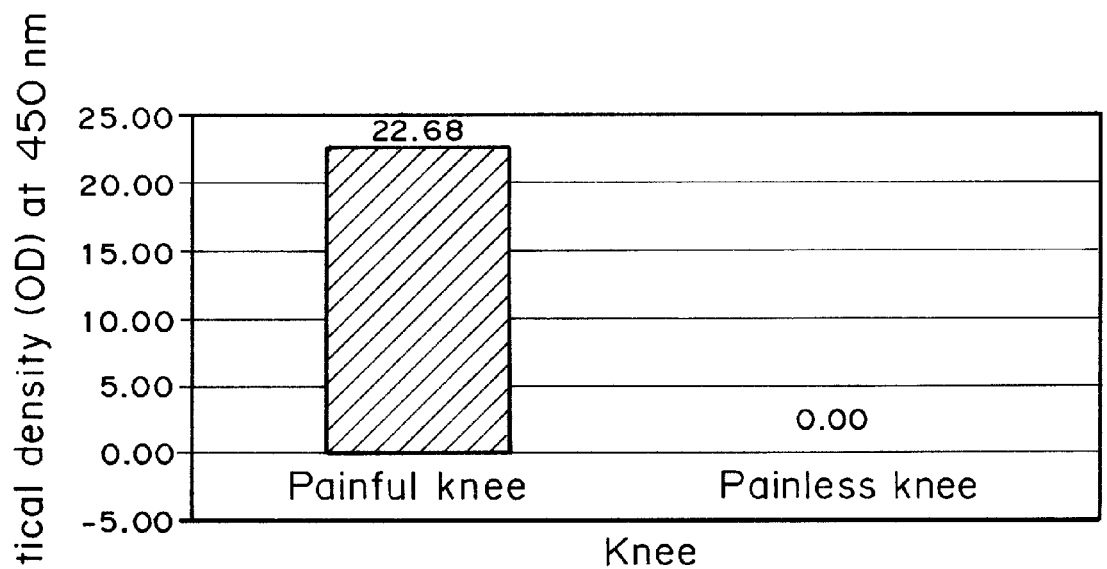
FIG. 6 is a bar graph comparing the optical density (OD) from a heterogeneous ELISA assay for fibronectin-aggrecan (G3) from the asymptomatic control knees to the symptomatic painful knees of a single human subject.

Results:

Twelve (12) symptomatic knees and ten (10) asymptomatic knees were assayed according to protocol. The mean (±standard deviation) optical density (OD) of the symptomatic group was 1.82 (±0.50) and of the asymptomatic control group was −0.12 (±0.07). This difference is statistically significant by t-test (p<0.001). FIG. 6 demonstrates the results for each symptomatic patient and asymptomatic control.

This example demonstrates a complex of fibronectin-aggrecan (G3) can be assayed from the synovial fluid of the knee joint and serve as a biomarker to predict the presence of intra-articular derangement as diagnosed by history, physical examination, and MRI scanning.

Example 9

Comparison of Synovial Fluid Samples from One Painful Knee to the Contralateral Asymptomatic Knee in a Single Human Subject To compare the utility of the fibronectin-aggrecan (G3) complex as a biomarker for the presence of pain in a synovial joint, the synovial fluid of the painful knee was compared to the synovial fluid of the contralateral asymptomatic knee from a single human subject. This paired comparison eliminates the inter-subject variability of unmatched case-control studies.

Materials and Methods:

After obtaining institutional review board approval, a single subject was recruited into a study with a matched case control design. He gave informed consent to participate. The subject was a 47 year old male, with activity related pain of one knee. He had failed conservative management (injections, therapy) and had an MRI positive for meniscal tear. There was no fracture of either knee or inflammatory arthritides, ligament injury, or oral/intra-articular steroid injection within 3 months of surgery date for the painful knee. The contralateral asymptomatic knee was free of significant pain or history of intermittent pain or surgery. The exam of the asymptomatic knee was normal and there was no history of prior surgery.

Two intra-articular samples were collected as described in example 6: one from the painful knee and one from the asymptomatic knee. The aspirates were aliquoted into eppendorf tubes containing protease inhibitor cocktail then placed on ice until transport. A heterogeneous ELISA assay for the presence of fibronectin-aggrecan (G3) complex (i.e. as described in example 4) was performed on each sample after dilution in a 1:10 ratio.

Results:

The optical density of the painful knee was 22.68 at 450 nanometers (nm) wavelength. The optical density of the non-painful knee was 0.00 at 450 nanometers (nm) wavelength, up to two decimal digits of precision after subtracting the blank value. FIG. 6 demonstrates the results for in bar graph format.

This example demonstrates a complex of fibronectin-aggrecan (G3) can be assayed from the synovial fluid of the knee joint and serve as a biomarker to predict the presence of intra-articular derangement as diagnosed by history, physical examination, and MRI scanning, even when experimentally controlling for variability by assaying the contralateral knees of a single human subject.

Example 10

Comparison of Synovial Fluid Samples from Painful Ankles Undergoing Total Ankle Arthroplasty to an Asymptomatic Control Ankle In order to compare the utility of the fibronectin-aggrecan (G3) complex as a biomarker for the presence of pain in a synovial joint, the synovial fluid of painful ankles in patients undergoing total ankle arthroplasty was compared to the synovial fluid of the ankle of an asymptomatic volunteer.

Materials and Methods:

After obtaining institutional review board approval, subjects were recruited into study with a case-control series design. All subjects gave informed consent to participate. Subjects with a painful ankle undergoing total ankle arthroplasty were recruited from the practice of a single foot and ankle surgeon in private practice. Inclusion criteria included in the age range 40-70 years, activity related ankle pain, failed conservative management (injections, therapy), plain radiographs positive for degenerative joint disease and osteoarthritis. Exclusion criteria included the presence of acute fracture, inflammatory arthritides (e.g. rheumatoid arthritis), or oral/intra-articular steroid injection within 3 months of surgery date.

A separate set of subjects was recruited from asymptomatic volunteers without ankle pain but with an age matched demographic. Inclusion criteria included age range 30-69 and the absence of ankle pain or an intermittent history of ankle pain. Exclusion criteria included inflammatory arthritides, oral/intra-articular steroid injection, or a physical examination of ankle alignment and stability outside the range of normal limits.

For each subject, an intra-articular sample was collected as follows. The aspiration site was prepped with triple preparation of chlorhexidine gluconate and aspiration was performed from an anterior approach with a sterile 10 cc syringe and a 21 gauge×1.5 inch needle. The ankle was lavaged with 2 cc of 0.9% normal saline, then the aspirate was withdrawn into the syringe. The aspirate was aliquoted into an eppendorf tube then placed on ice until transport.

A heterogeneous ELISA assay for the presence of fibronectin-aggrecan (G3) complex (i.e. as described in example 4) was performed on each sample after dilution in a 1:5 ratio.

Results:

Four (4) symptomatic ankles and one (1) asymptomatic ankle were assayed according to protocol. The mean (±standard deviation) optical density (OD) of the symptomatic group was 8.4 (±5.1) and of the asymptomatic volunteer was 0.0.

This example demonstrates a complex of fibronectin-aggrecan (G3) can be assayed from the synovial fluid of the ankle joint and serve as a biomarker to predict the presence of intra-articular derangement and degenerative joint disease as diagnosed by history, physical examination, and plain radiography scanning.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

We claim:

1. A kit for detecting complexes of fibronectin and aggrecan or fragments thereof in a sample, said fibronectin/aggrecan complexes comprising fibronectin or a fragment thereof and aggrecan or a fragment thereof, said kit comprising:
   (a) either a detection binding partner that binds selectively to a fibronectin/aggrecan complex or a combination of separate first and second detection binding partners, wherein said first binding partner binds to fibronectin or a fragment thereof and said second binding partner binds to aggrecan or a fragment thereof; and
   (b) a positive control, wherein the positive control comprises an isolated fibronectin/aggrecan complex.

2. The kit of claim 1,
   wherein the kit comprises a combination of first and second binding partners, wherein one of said binding partners is a capture binding partner bound to a substrate and said capture binding partner selectively binds to either fibronectin or a fragment thereof or to aggrecan or a fragment thereof.

3. The kit of claim 2, wherein the first binding partner is a capture binding partner.

4. The kit of claim 2, wherein the second binding partner is a capture binding partner.

5. The kit of claim 2, wherein the first and second binding partners are selected from the group consisting of an antibody or an antigen-binding fragment thereof, a fibronectin-aggrecan complex receptor or fragment thereof capable of binding fibronectin-aggrecan complexes, or any combination thereof.

6. The kit of claim 1 wherein said positive control comprises an isolated fibronectin/aggrecan complex wherein said fibronectin or fragment thereof and said aggrecan or fragment thereof are from the same or different species.

7. The kit of claim 1, wherein the positive control comprises a G1, IGD, G2, KS, CS1, CS2 or G3 domain of aggrecan, a fibronectin-binding fragment thereof, or any combination thereof.

8. The kit of claim 1, wherein the positive control comprises an aggrecan-binding fragment of fibronectin.

9. The kit of claim 1, wherein the fibronectin, aggrecan, or fragments thereof in said positive control are recombinant, natural, or any combination thereof.

10. The kit of claim 1, further comprising a device for obtaining a biological sample from a subject.

11. The kit of claim 1, wherein said positive control is present at a concentration higher than the concentration present in a sample from an uninjured subject.

12. The kit of claim 1, wherein the detection binding partner binds selectively to a fibronectin/aggrecan complex.

* * * * *